United States Patent
Waugh et al.

(10) Patent No.: US 10,575,983 B2
(45) Date of Patent: Mar. 3, 2020

(54) MEDICAL DEVICES FOR GENERATING HEAT AND METHODS OF TREATMENT USING SAME

(71) Applicant: Candesant Biomedical, Inc., Palo Alto, CA (US)

(72) Inventors: Jacob M. Waugh, Newark, CA (US); Christopher Elkins, Redwood City, CA (US); Hyop Rhee, Morgan Hill, CA (US)

(73) Assignee: Candesant Biomedical, Inc., San Francisco, CA (US)

(*) Notice: Subject to any disclaimer, the term of this patent is extended or adjusted under 35 U.S.C. 154(b) by 685 days.

(21) Appl. No.: 15/048,052

(22) Filed: Feb. 19, 2016

(65) Prior Publication Data
US 2016/0242959 A1     Aug. 25, 2016

Related U.S. Application Data

(60) Provisional application No. 62/259,315, filed on Nov. 24, 2015, provisional application No. 62/176,907, filed on Feb. 19, 2015.

(51) Int. Cl.
*A61F 7/02*     (2006.01)
*A61F 7/03*     (2006.01)
(Continued)

(52) U.S. Cl.
CPC .............. *A61F 7/03* (2013.01); *A61B 18/06* (2013.01); *A61F 7/034* (2013.01); *A61F 7/12* (2013.01);
(Continued)

(58) Field of Classification Search
CPC ...... A61F 7/03; A61F 7/34; A61F 2007/0047; A61F 2007/0003; A61F 2007/0036;
(Continued)

(56) References Cited

U.S. PATENT DOCUMENTS 3,283,357 A * 11/1966 Decker ................ A47L 25/08
                                                          15/104.93
3,400,199 A     9/1968 Balassa
(Continued)

FOREIGN PATENT DOCUMENTS

EP     2151171 A1     2/2010
GB     1068667 A      5/1967
(Continued)

OTHER PUBLICATIONS

Rao et. al, Injectable liquid alkali alloy based-tumor thermal ablation therapy, Journal of Minimally Invasive Therapy & Allied Technologies, vol. 18, 2009—Issue 1, pp. 30-35 (Year: 2009).*
(Continued)

*Primary Examiner* — Kaitlyn E Smith
*Assistant Examiner* — Yasamin Ekrami
(74) *Attorney, Agent, or Firm* — McDermott Will & Emery LLP; Judy M. Mohr

(57) ABSTRACT

A device comprising a heat-generating component that comprises an alkali metal is provided. The alkali metal in the presence of water at a point of contact of the device undergoes an exothermic reaction to generate heat in situ. The amount of heat generated is proportional to and/or limited by the amount (or moles) of water at the point of contact, and the heat generated is sufficient to achieve an increase in temperature at the point of contact to achieve a therapeutic or beneficial result. In one embodiment, the device is used for reducing sweat production in a subject suffering from excessive sweating or hyperhidrosis. In other embodiments, the device is used to substantially sterilize a surface or render a surface substantially aseptic.

27 Claims, 19 Drawing Sheets

(51) Int. Cl.
*A61B 18/06* (2006.01)
*A61F 7/12* (2006.01)
*A61F 7/00* (2006.01)

(52) U.S. Cl.
CPC ............... *A61F 2007/0003* (2013.01); *A61F 2007/0006* (2013.01); *A61F 2007/0019* (2013.01); *A61F 2007/0022* (2013.01); *A61F 2007/0024* (2013.01); *A61F 2007/0036* (2013.01); *A61F 2007/0047* (2013.01)

(58) Field of Classification Search
CPC ...... A61F 2007/0024; A61F 2007/0006; A61F 2007/0019; A61F 2007/0022
See application file for complete search history.

(56) References Cited

U.S. PATENT DOCUMENTS

| | | | | |
|---|---|---|---|---|
| 3,941,128 | A * | 3/1976 | Baldwin | A61M 5/286 604/238 |
| 4,235,332 | A | 11/1980 | Andersen et al. | |
| 4,274,420 | A * | 6/1981 | Hymes | A61B 5/04087 600/391 |
| 4,303,546 | A | 12/1981 | Waegerle | |
| 4,382,304 | A * | 5/1983 | Lehmann | E03D 9/038 4/227.1 |
| 4,742,581 | A * | 5/1988 | Rosenthal | A41D 20/005 2/170 |
| 4,796,622 | A | 1/1989 | Lu et al. | |
| 5,879,378 | A | 3/1999 | Usui | |
| 6,099,556 | A | 8/2000 | Usui | |
| 6,465,709 | B1 | 10/2002 | Sun et al. | |
| 6,890,553 | B1 | 5/2005 | Sun et al. | |
| 6,960,225 | B1 | 11/2005 | Zenz et al. | |
| 7,084,102 | B1 * | 8/2006 | Arnau | C11D 3/1253 510/294 |
| 7,097,642 | B1 | 8/2006 | Sprague et al. | |
| 7,531,080 | B2 | 5/2009 | Carson et al. | |
| 7,871,508 | B2 | 1/2011 | Carson et al. | |
| 7,883,640 | B2 | 2/2011 | Doona et al. | |
| 2001/0010847 | A1 * | 8/2001 | Otsuka | A61F 7/034 428/36.1 |
| 2002/0045923 | A1 * | 4/2002 | Tone | A61F 7/034 607/96 |
| 2003/0019508 | A1 * | 1/2003 | Tomarchio | A47K 10/42 134/6 |
| 2004/0042965 | A1 * | 3/2004 | Usui | A61F 7/034 424/40 |
| 2004/0077513 | A1 * | 4/2004 | Lefenfeld | A61L 9/05 510/191 |
| 2004/0146620 | A1 | 7/2004 | Iwashita et al. | |
| 2005/0000828 | A1 | 1/2005 | Carson et al. | |
| 2005/0161342 | A1 | 7/2005 | Carson et al. | |
| 2005/0288646 | A1 * | 12/2005 | LaVon | A61F 13/4942 604/385.28 |
| 2006/0097222 | A1 | 5/2006 | Doona et al. | |
| 2007/0099812 | A1 * | 5/2007 | Luizzi | A61K 8/0208 510/438 |
| 2007/0267595 | A1 * | 11/2007 | Dodo | A61F 7/034 252/67 |
| 2008/0140165 | A1 | 6/2008 | Cohen et al. | |
| 2009/0062890 | A1 * | 3/2009 | Ugajin | A61F 7/034 607/104 |
| 2009/0181157 | A1 * | 7/2009 | Toreki | A01N 33/12 427/2.3 |
| 2010/0196343 | A1 * | 8/2010 | O'Neil | A61B 18/203 424/94.4 |
| 2011/0106227 | A1 * | 5/2011 | Desiderio | A61F 7/02 607/111 |
| 2012/0022621 | A1 | 1/2012 | Wong et al. | |
| 2013/0074860 | A1 * | 3/2013 | Colvan | A61K 8/365 132/200 |
| 2013/0260623 | A1 | 10/2013 | Oh | |
| 2014/0206947 | A1 | 7/2014 | Isserow et al. | |
| 2015/0184891 | A1 * | 7/2015 | Oka | A61F 7/034 126/263.05 |
| 2016/0213294 | A1 * | 7/2016 | Patton | A61B 5/150343 |

FOREIGN PATENT DOCUMENTS

| | | |
|---|---|---|
| GB | 2297490 | 8/1996 |
| WO | WO 2002/006421 A1 | 1/2002 |

OTHER PUBLICATIONS

Rao et al., Tumor thermal ablation therapy using alkali metals as powerful self-heating seeds; Minimally Invasive Therapy, 2008; 17:1; 43-49) (Year: 2008).*
Hamm et al., "Primary focal hyperhidrosis: disease characteristics and functional impairment", Dermatology, vol. 212, No. 4, pp. 343-353 (2006).
Hornberger et al., "Recognition, diagnosis, and treatment of primary focal hyperhidrosis", J. Am. Acad. Dermatol., vol. 51, No. 2, pp. 274-286 (2004).
Naumann et al., "Effect of botulinum toxin type A on quality of life measures in patients with excessive axillary sweating: a randomized controlled trial", Br. J. Dermatol., vol. 147, No. 6, pp. 1218-1226 (2002).
Strutton et al., "US prevalence of hyperhidrosis and impact on individuals with axillary hyperhidrosis: results from a national survey", J. Am. Acad. Dermatol., vol. 51, No. 2, pp. 241-248 (2004).
Theale et al., "Development, validity, and reliability of the Hyperhidrosis Impact Questionnaire (HHIQ)", Qual. Life Res., vol. 11, No. 7, pp. 619 and 702, Abst. # 324 (2002).
International Search Report from PCT Patent Application No. PCT/US2016/018655 dated May 23, 2016.

* cited by examiner

0 Hours

24 Hours

48 Hours

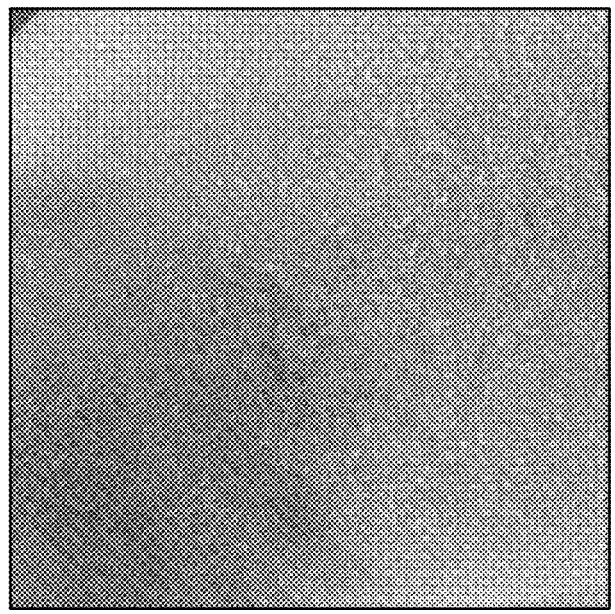
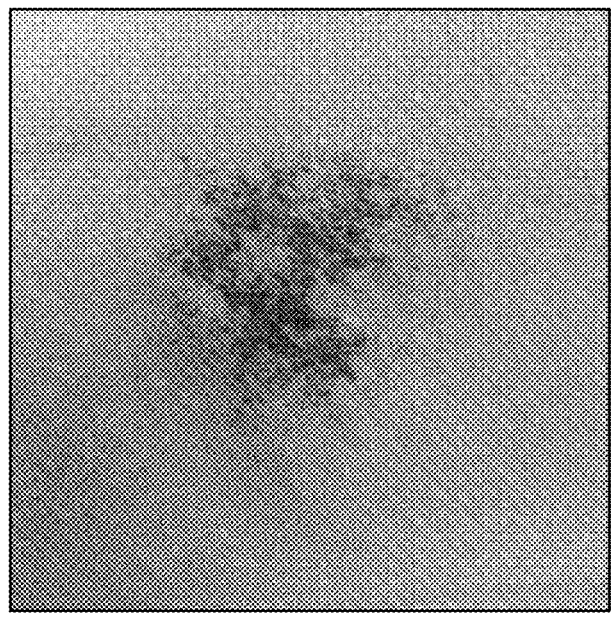
FIG. 6A
FIG. 6B

MEDICAL DEVICES FOR GENERATING HEAT AND METHODS OF TREATMENT USING SAME

CROSS-REFERENCE TO RELATED APPLICATIONS

This application claims the benefit of U.S. Provisional Application No. 62/176,907, filed Feb. 19, 2015 and of U.S. Provisional Application No. 62/259,315, filed Nov. 24, 2015, both incorporated herein by reference in their entirety.

TECHNICAL FIELD

Devices comprising a substrate and an alkali metal for generating heat are described, where heat is produced in situ. Methods for using the devices in medical and cosmetic situations are described.

BACKGROUND

Devices that rely on an exothermic reaction as a self-contained heat source are familiar to consumers in the form of, for example, disposable hand and foot warmers. These devices include a reaction mixture that generates heat when water or oxygen is introduced into the reaction mixture. Devices that produce heat are also used in medical situations, such as in the ablation of tissues or cells, to cauterize wounds, and to render various surfaces substantially aseptic. Cauterization is a medical technique used to stop blood flow and help seal the surface of a wound. Various conventional devices for carrying out cauterization include electrocauterizers and laser cauterizers that act to destroy tissue while rapidly aiding the coagulation of blood vessels which have been cut in the wound. These devices do not typically rely on an exothermic chemical reaction as the source of heat.

Heat can also be used to render surfaces aseptic. For example, a variety of devices and methods have been used to sterilize surgical instruments (such as autoclaves) and other surfaces, such as a patient's skin or a surgeon's hands, and examples of such devices that are non-heat based include antiseptic wipes, antibacterial solutions, etc. Sterilization techniques for instruments generally use heat for extended periods of time as an aid in destroying bacterial and other pathogens on the instruments. Sterilization techniques for use with human skin or other surfaces typically rely on a chemical interaction between the material being applied and the pathogens themselves to destroy the pathogens.

Medical systems such as bandages are conventionally used to slow bleeding by providing pressure to a wound and by assisting with the blood's natural coagulation process that involves platelets in the blood and fibrin. Bandages are also used to help prevent additional bacterial and other harmful materials from entering an open wound. Bandages used to cover wounds generally include a portion either directly coupled to the bandage or coupled to the wound through the bandage that is sterile, such as a gauze pad or other sterile structure.

BRIEF SUMMARY

In a first aspect, a device is provided, the device comprising a substrate having a first surface and a second surface and an alkali metal in contact with the substrate. The alkali metal is selected from sodium and potassium and is present in an amount sufficient to generate an amount of heat in situ when the substrate contacts a surface to bring the alkali metal in contact with water at a point of contact between the alkali metal and the surface.

In one embodiment, the first surface of the substrate is a first planar surface and the second surface of the substrate is an opposing planar surface.

In another embodiment, the first planar surface is a contact surface or distal surface for contact with a surface to receive heat.

In another embodiment, the opposing planar surface is a proximal surface in which the alkali metal is in contact.

In yet another embodiment, the alkali metal is embedded in or integral with the substrate.

In still another embodiment, the alkali metal forms a layer on the substrate.

In another embodiment, the alkali metal forms a discontinuous layer on the substrate.

In other embodiments, the alkali metal forms the layer or the discontinuous layer on the second surface of the substrate.

In still other embodiments, the alkali metal is in contact with a portion of the substrate.

In yet another embodiment, the substrate is a mesh having open regions, also referred to as interstitial regions or open spaces, and the alkali metal is embedded in a portion of the open regions.

In one embodiment, the amount of heat generated is limited by the amount of or moles of alkali metal.

In another embodiment, the amount of heat generated is limited by the amount of or moles of water at the site of contact.

In yet another embodiment, the amount of heat generated is proportional to moles of water present at the site of contact.

In still another embodiment, the heat generated is limited by the amount of or moles of water at the site of contact.

In one embodiment, the heat generated is proportional to the amount of or moles of water at the site of contact.

In another embodiment, the amount of heat is generated in situ at the site of contact is in proportion to the moles of water present at site of contact.

In one embodiment, the alkali metal is neat sodium.

In other embodiments, the alkali metal is an alloy of sodium or an alloy of potassium.

In yet another embodiment, the alkali metal is a sodium/potassium alloy

In still another embodiment, the alkali metal is an oxide of potassium or an oxide of sodium.

In one embodiment, the substrate is a paste.

In another embodiment, the substrate is an anhydrous aluminum containing paste.

In another embodiment, the substrate is a metal substrate or metal alloy substrate.

In other embodiments, the metal substrate is a stainless steel mesh.

In other embodiments, the substrate is a woven substrate.

In still other embodiments, the substrate has a water impermeable layer.

In a second aspect, a kit, comprising a device as described herein, a wipe comprising a solvent; and instructions for use, is provided.

In one embodiment, the solvent is isopropyl alcohol.

In another embodiment, the kit further comprises a gauze.

In a third aspect, a method for treatment of a condition is provided. The method comprises applying at a site of contact a substrate comprising an amount of an alkali metal selected from sodium and potassium to generate heat in situ in an amount sufficient to treat the condition.

In one embodiment, the heat is generated by an exothermic reaction of the alkali metal and water in situ at the site of contact.

In one embodiment, the condition is hyperhidrosis. In another embodiment, the condition is perceived excessive sweating.

In certain embodiments, the condition is a wound, or the condition is a symptom associated with seasonal allergies or perceived seasonal allergies seasonal allergies. The symptom, in one embodiment, is a runny nose.

In yet another aspect, a method for treatment of excessive sweating is provided. The method comprises contacting a substrate comprising an amount of an alkali metal selected from sodium and potassium with a site of contact on skin of a subject to generate heat in situ in an amount sufficient to treat the condition. In one embodiment, the method comprises contacting a substrate comprising an amount of an alkali metal selected from sodium and potassium with a site of contact on skin of a subject to generate heat in situ at the site of contact by an exothermic reaction of the alkali metal and water in situ at the site of contact.

In one embodiment, the excessive sweating is associated with hyperhidrosis.

In another embodiment, the condition is moderate to severe hyperhidrosis. In one embodiment, the moderate to severe hyperhidrosis is assigned based on the hyperhidrosis disease severity scale.

In one embodiment, the excessive sweating is perceived excessive sweating.

In another embodiment, the subject is a male subject.

In other embodiments, the site of contact is an underarm (axilla). In other embodiments, the site of contact is on a position on the subject selected from a palm of a hand, a sole of a foot, a face, a back, a chest or an abdomen.

In one embodiment, contacting is done once per week for a period of about one month. In other embodiments, contacting is done once per week for a period of between about 1 month to about 12 months.

In yet another embodiment, contacting achieves a temporary reduction in sweat production, as measured subjectively by the patient or as measured by an assessment scale or gravimetrically.

In another aspect, a method for treatment of a wound is provided. The method comprises contacting a substrate comprising an amount of an alkali metal selected from sodium and potassium with a site of contact on skin of a subject to generate heat in situ in an amount sufficient to treat the wound. In one embodiment, contacting comprises contacting a substrate comprising an amount of an alkali metal selected from sodium and potassium with a site of contact on skin of a subject to generate heat in situ at the site of contact by an exothermic reaction of the alkali metal and water in situ at the site of contact.

In one embodiment, the wound is a subcutaneous wound associated with a surgical procedure.

In another embodiment, applying cauterizes skin at the point of contact to close/seal the wound.

In yet another embodiment, applying sterilizes the point of contact.

In still another embodiment, uninjured skin adjacent injured/wounded skin exposed to the device is not visually altered by the treatment.

In yet another aspect, a method for attenuation or treatment of a symptom associated with seasonal allergies or with perceived seasonal allergies is provided. The method comprises contacting a substrate comprising an amount of an alkali metal selected from sodium and potassium with a site of contact in nasal tissue of a subject to generate heat in situ in an amount sufficient to treat the heat the nasal tissue and attenuate or the symptom. In one embodiment, contacting comprises contacting a substrate comprising an amount of an alkali metal selected from sodium and potassium with a site of contact in nasal tissue of a subject to generate heat in situ at the site of contact by an exothermic reaction of the alkali metal and water in situ at the site of contact in an amount sufficient to treat the heat the nasal tissue and attenuate or the symptom.

In one embodiment, the symptom is a runny nose.

In various embodiments of the aspects detailed herein, the amount of heat generated in situ relates to, is controlled by, is proportional to, and/or is limited by an amount of water at the point of contact.

In another embodiment of the aspects detailed, the oxidizing material is not Fe, Al, Mg, Zn or C.

In other embodiments of the aspects detailed, the device is non-invasive.

In other embodiments of the aspects detailed, the alkali metal is not in the form of particles coated or encapsulated or encased with a polymer In other embodiments of the aspects detailed, the carrier is non-sticky and cannot and/or does not adhere to a skin surface.

In other embodiments of the aspects detailed, the heat generated produces a temperature profile at the point of contact, and the temperature profile is not constant over any 3 minute interval, 1 minute interval, or 2 minute interval, during a period of contact between the substrate and the surface.

The foregoing and other aspects, features, and advantages will be apparent to those artisans of ordinary skill in the art from the description, drawings and the claims.

BRIEF DESCRIPTION OF THE DRAWINGS

FIG. 6A is a photograph of the axilla of a patient after 90 seconds following stain testing; and FIG. 6B is a photograph of the axilla of the patient of FIG. 6A following treatment with an aluminum salt suspension containing NaK at 90 seconds following stain testing.

DETAILED DESCRIPTION

Figure 1A:
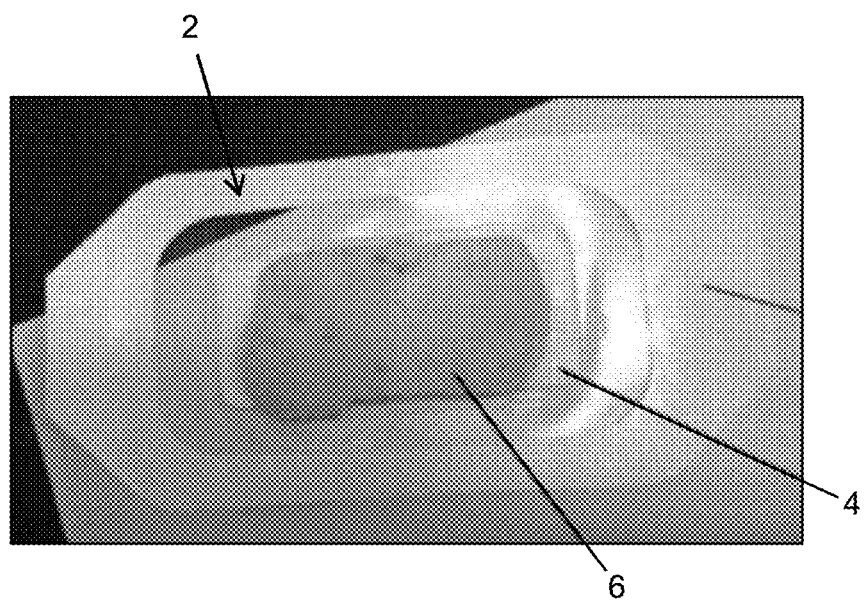
FIG. 1A is a photograph of a device according to one embodiment, where the device is in the form of a bandage comprising a substrate with a composition comprising solid sodium metal coupled to the substrate.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms and "the" include plural referents unless the context clearly dictates otherwise.

I. DEVICES

In one aspect, devices comprising a component for generating heat are provided. The component that generates heat comprises a substrate and an alkali metal. This component of the devices is now described.

The alkali metal is present in the devices in an amount sufficient to generate heat. As used herein an 'alkali metal' intends a univalent (monovalent) metal belonging to group 1A of the periodic table, including potassium, sodium, lithium, rubidium, cesium and francium. Reference to 'alkali metal' or to one of the specific metals, e.g., potassium metal or sodium metal, include its salts, oxides, peroxides, superoxides, hydroxides, halides, and the like, provided the alkali metal in the presence of water undergoes an exothermic reaction. Reference to an 'alkali metal' also includes alloys that comprise one or more alkali metals.

In one embodiment, the alkali metal is potassium or sodium. In another embodiment, the alkali metal is a neat alkali metal, sometimes referred to as the free metal, such as potassium free metal or sodium free metal. In other embodiments, the alkali metal is potassium or sodium in the form of an oxide. Sodium monoxide ($Na_2O$) and sodium peroxide ($Na_2O_2$) and sodium superoxide ($NaO_2$) are examples. Sodium metal is a soft metal that is highly reactive with oxygen and water. Sodium metal can be cut, broken up, and shaped into various forms due to its softness. Potassium metal is likewise a soft metal that has higher reactivity with oxygen and water than does sodium metal.

In another embodiment, the alkali metal is an alloy, such as an alloy of sodium and potassium. Sodium metal and potassium metal can be combined to form a sodium/potassium alloy (NaK) which is a liquid at room temperature. NaK that is liquid at room temperature contains between about 40% to about 90% potassium by weight. A eutectic between sodium and potassium occurs at about 77% potassium and about 23% sodium and the liquid metal at the eutectic point is less dense than water. Eutectic compositions may be used in various embodiments of the devices described herein, as well as any combination of sodium and potassium in proportions that form a stable alloy. Accordingly, the term "NaK" is used herein to refer to a sodium and potassium alloy, as used herein, this term represents any possible combination of sodium and potassium and not just a 50/50 atomic mixture and not just a eutectic composition.

Sodium metal when contacted by water generates hydrogen gas and heat according to the following reaction:

$$2Na(s)+2H_2O(l) \rightarrow 2NaOH(l)+H_2(g)+184\ kJ$$

For sodium metal 4.0 MJ/kg of Na(s) can be generated directly and 5.3 MJ/kg Na(s) is generated from combustion of the hydrogen gas with oxygen. The reaction involves equimolar amounts (that is, equal numbers of atoms or molecules) or the alkali metal (e.g., sodium) and water to form a mole of alkali metal hydroxide and half a mole of hydrogen gas and heat. Accordingly, a large amount of heat from a relatively small amount of sodium metal is generated. The reaction stops when the alkali metal (e.g., sodium metal) is fully consumed, thus the amount of heat generated can be directly calculated and controlled by the amount of metal involved in the reaction. Similar reactions that release relatively large amounts of heat also occur for potassium metal and for NaK alloys when contacted with water, and the amount of heat generated is controllable by the amount of alkali metal and/or by the amount of water available for reaction with the alkali metal.

Because of the large amount of heat generated through the reaction of alkali metals, such as sodium, potassium, and NaK, with water, devices comprising one or more of these metals can be used in medical and cosmetic procedures where heat provides a beneficial therapy or effect, as will be further described below. The exothermic reaction generates in some cases sodium hydroxide, and a buffering component may optionally be used in conjunction with the alkali metal to neutralize the sodium hydroxide, causing the effects of the composition to be the result of heat generation. The heat generated by the alkali metal depends, in part, upon the amount available for reaction, the amount of water at a point of contact on a surface available for reaction, and (in some cases) the way in which the alkali metal is contacted with a surface (e.g., wound or skin) for contact with water present at the surface. The alkali metal may be mixed with other compounds and/or metals to control the heat release properties, reactivity, shapeability, or other physical characteristic of the alkali metal, if desired.

In the device, the alkali metal is typically formed on, in contact with, incorporated into, or associated with a base or a substrate. The base or substrate is preferably inert and does not contribute to or deter the exothermic reaction that occurs when the alkali metal contacts water. The terms "base" and "substrate" are used interchangeably herein, and this element of the heating component functions to support and/or carry the alkali metal. Several non-limiting examples for purposes of illustration are provided herein, and a wide variety of base designs can be constructed using the principles disclosed herein.

In one embodiment, the base is a dermal pen or dermal roller, and the alkali metal (e.g., the sodium metal or potassium metal or NaK alloy) is held within the dermal pen or dermal roller. The dermal pen or dermal roller is then subsequently used to contact the alkali metal with a patient's skin. In another embodiment, the dermal roller is a hot roller, and may be configured for use by a patient on their own or for use by a doctor or other medical staff in a medical office. In other embodiments, the base is a bandage and the alkali metal, (e.g., sodium metal, potassium metal, or NaK) is included in a sterile dressing coupled to the bandage. In other implementations, the alkali metal (sodium metal, potassium metal, or NaK) is included on the surface of the sterile dressing.

In another embodiment, the substrate is a needle, a wipe or a sponge, and devices using these substrates are further described below. Devices using a needle contemplate hollow needles and solid needles, where the alkali metal is a coating on the external surface of the needle or, for hollow needles, in the annual space of the needle. Devices using a wipe or a sponge as the substrate contemplate porous and non-porous materials where the alkali metal forms a layer on the substrate, is embedded in pores or openings in the substrate, or a combination of both a layer and embedded in pores.

In another embodiment, the substrate is a planar substrate having opposing sides. That is, the planar substrate has a first side and a second side. In other embodiment, the substrate has a first side and a second side, and is non-planar. In embodiments where the substrate has a first side and a second side, the first side may be referred to as a distal surface or a contact surface. The contact surface intends the surface of the substrate that contacts a surface to receive heat during use of the device, as described below. The second side of the substrate may be referred to as a proximal surface. The proximal surface is in contact with, supports, or carries the alkali metal and/or is in contact with a backing member on the device if such a member is desired or needed. The alkali metal on the substrate may cover the entire substrate or may cover a portion of the substrate. The alkali metal on the substrate may be a discontinuous layer disposed on or in all or a portion of the substrate, or may be a continuous layer on or within all or a portion of the substrate. In one embodiment, the substrate is a woven material, and in another embodiment it is a non-woven material. In some of the exemplary embodiments described in the working examples below, the substrate is a mesh, i.e., a material having open regions (interstitial regions or open spaces) in a network of fibers. The alkali metal is embedded in all or a portion of the open regions of the mesh substrate.

The material forming the substrate is preferably one that is inert in the presence of the exothermic reaction and its reactants and is stable in the presence of the heat generated. Non-limiting examples include metals, such as iron, copper, zinc, nickel, palladium, platinum, gold, titanium. The metal may be treated by painting, anodizing or plating. The substrate may also be a metal alloy, such as alloys of iron (e.g., steel, stainless steel, cast iron, alloy steel), allows of aluminum, titanium, copper (e.g., bronze) and magnesium. Steel are alloys of iron and other elements, primarily carbon. Stainless steel is a steel alloy with chromium, the latter typically present at a minimum of 10.5 wt % of the alloy composition. Other examples of materials for forming the substrate include heat resistant fabrics and/or fire retardant fabrics, such as those sold under the tradenames KOVENEX® and NOMEX®. Exemplary materials in heat-resistant fabrics include fiberglass, polyesters, imidazole based polymers like polybenzimidazole, aramid based polymers like polyaramid, amorphous silica cloth, silic cloth with cured silicon rubber on one side, aluminized polyester, composites of polymers and fiberglass (such as a composite of aramid and fiberglass fibers), aluminized cloth, aluminized polyester, cloth of stainless steel wire, cloth of a brass wire plied with fiberglass yarns, and the like. Materials may also be topically treated with a chemical, such as with polytetrafluoroethylene, to render the material heat resistant or fire retardant.

As mentioned above, the base may take the form of a knife or blade. In this embodiment, the alkali metal may be in the form of a coating or layer on the surface of the knife or blade. Surgical scalpels or knives are one example, where the alkali metal forms a coating or layer on the edge of the scalpel or knife used to contact the skin, where it is desirable for the wound being created by the scalpel or knife to be cauterized through reaction of the alkali metal coating with the water in the blood or tissue at the site of wound creation. Other applications with bases having coatings include sticks that can be used in surgery to cauterize wounds during the surgical process simply by inserting the stick into the wound and contacting it with the surface of the wound. Coatings could also be used on dermal rollers, needles, and other surgical instruments where the ability to cauterize a wound on contact is desired.

In another embodiment, the substrate or base is in the form of a semi-solid or solid composition or mixture of ingredients in which the alkali metal is dispersed, dissolved, or carried. For example, a base in the form of a semi-solid composition comprising ingredients in conventional antiperspirants or deodorants that are applied to the axilla is contemplated, where the alkali metal is admixed with the ingredients forming the semi-solid composition. A base may also be in the form of a paste or a thixotropic paste that is applied to a surface. Many make-ups in the cosmetic industry are pastes or thixotropic pastes, and ingredients for forming such compositions are known. Additional of alkali metal to the pastes is contemplated, for example, by addition of a powdered alkali metal. The paste can then be smeared onto the surface.

Because the alkali metal in the heat generating component may react with the oxygen in air, the base and/or heat generating component may contain various features or structures designed to prevent contact between the alkali metal until the time for its use. For example, where the base is a knife, the knife may be placed in a container with an airtight lid or peelable covering with an inert gas, such as nitrogen or argon, contained therein. When the knife is needed, the knife may then be removed from the container and used before the reaction between the alkali metal and oxygen progresses sufficiently to impact the effectiveness of the knife to generate heat in situ in response to water at the point of contact upon use. Those of ordinary skill will readily be able to develop various protective structures and systems designed to minimize or prevent contact between the alkali metal and oxygen or moisture in the air using the principles disclosed herein.

A. Exemplary Devices

Devices comprising a heat-generating component comprised of a substrate and an alkali metal, as detailed above, are described with reference to the drawings and the examples. In a first embodiment, a device for cauterizing wounds is contemplated, where the device comprises a base (or substrate) having an alkali metal, such as potassium metal, sodium metal, or NaK, deposited on the base, coupled to the base, incorporated into the base, and/or associated with the base. FIG. 1A illustrates a device for cauterizing wounds, where the device is in the form of a bandage 2 comprising a that supports an amount of an alkali metal, in this example sodium free metal 6, formed into a sheet or layer and coupled to the substrate. The embodiment in FIG. 1A illustrates the softness and ductility of the alkali metal and how it can be shaped to correspond with various desired shapes in devices, such as in the illustrated bandage.

Figure 1B:
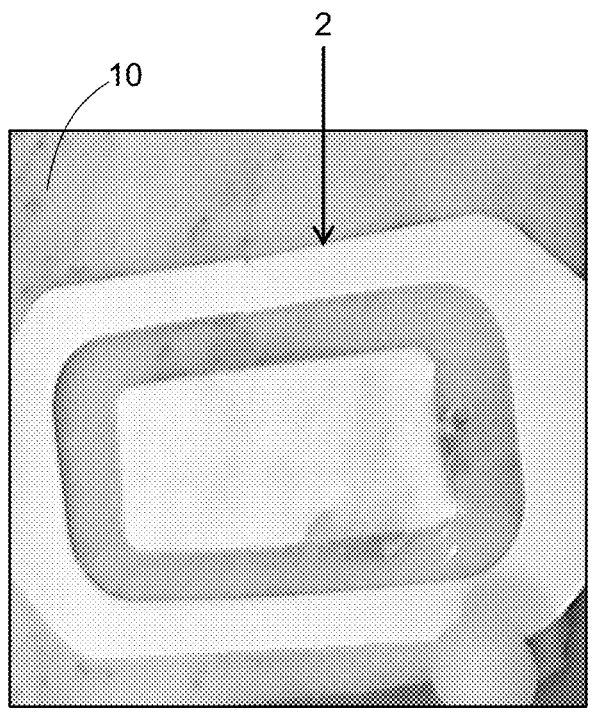
FIG. 1B is a photograph of the bandage-like device of FIG. 1A applied to a skin surface, the device applied to that the heat-generating component contacts an injured skin region and an intact skin region.

A study was conducted to illustrate use of the device in wound closure for improved or accelerated wound healing. With reference to Example 1, sodium metal 6 was coupled to substrate 4 using petroleum jelly to form a heat-generating component. The device was bought into contact a wound on skin. As a control, a portion of the device was contacted with a portion of the skin with no wound, i.e., uninjured, intact skin. FIG. 1B shows the device applied over the skin 10. The device was placed on the wound and on the intact, uninjured skin for 15 seconds, whereupon it was removed and the effect of the heat generated by the exothermic reaction between the sodium metal and water at the contact site was observed. The macroscopic appearance by unaided visual inspection and the micrographic appearance of both the uninjured skin tissue and the wounded tissue were observed. Photographs from the micrographic inspection are shown in FIGS. 1C-1J.

Figure 1C:
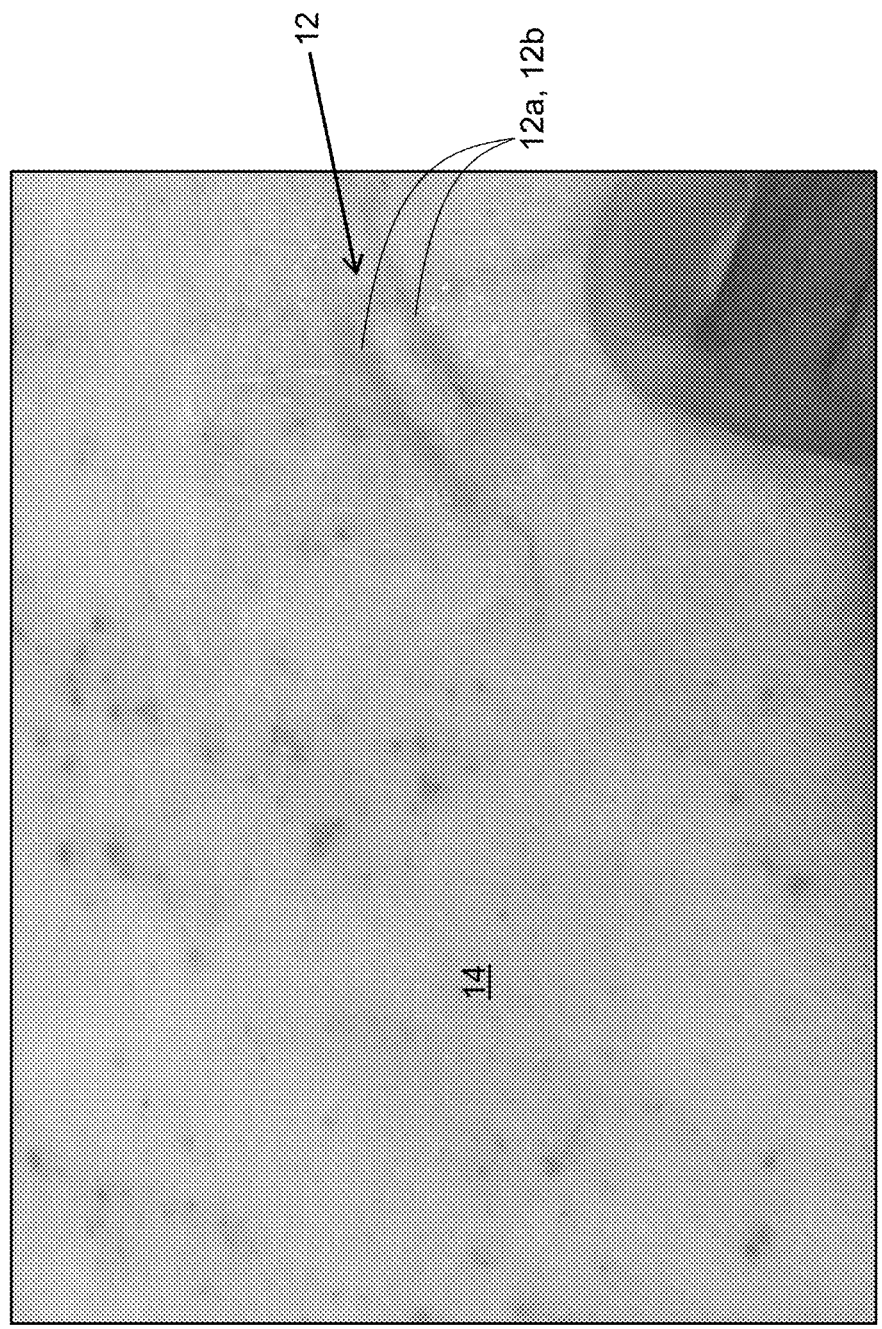
FIG. 1C is a photograph of the uninjured skin region and the wounded skin region, showing a first wound and a second wound, following application of the bandage-like device.
Figure 1D:
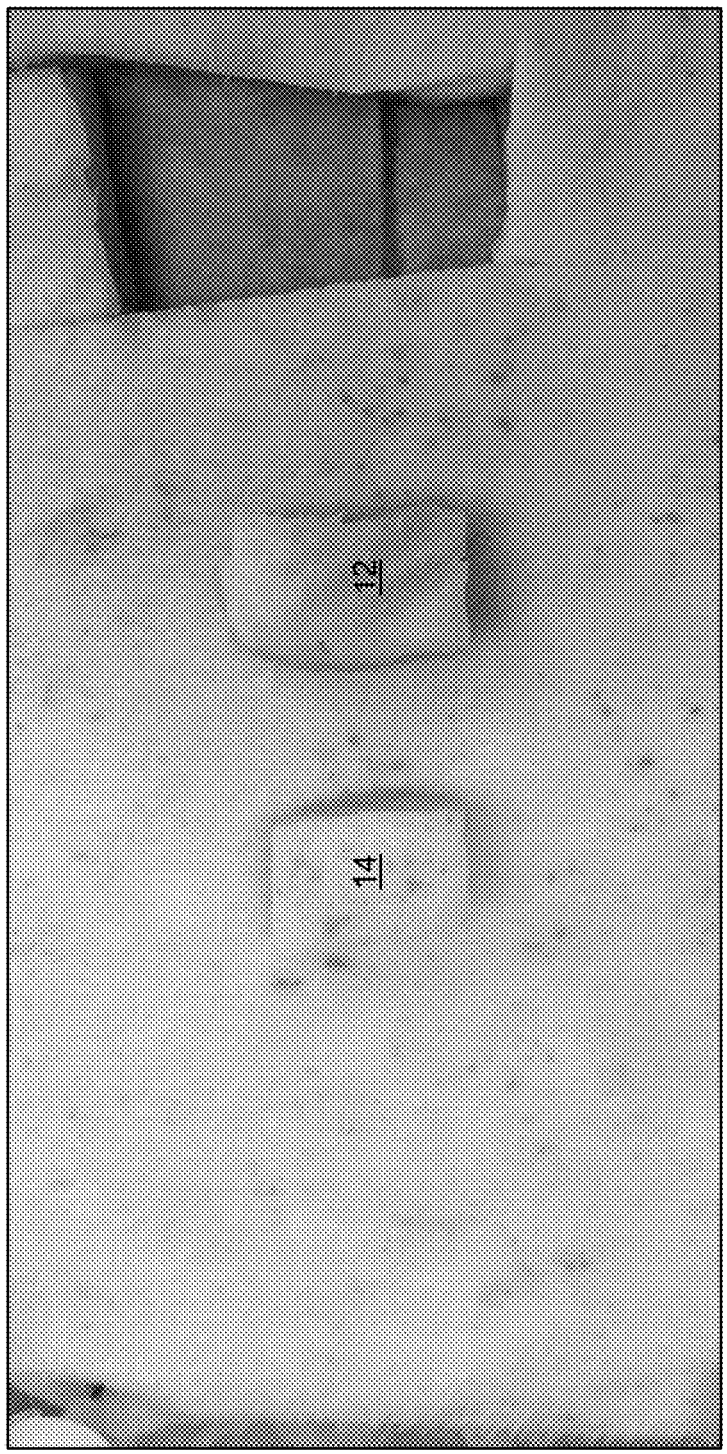
FIG. 1D is a photograph of two portions of the skin of FIG. 1C showing a portion that was uninjured and a portion that was wounded.
Figure 1E:
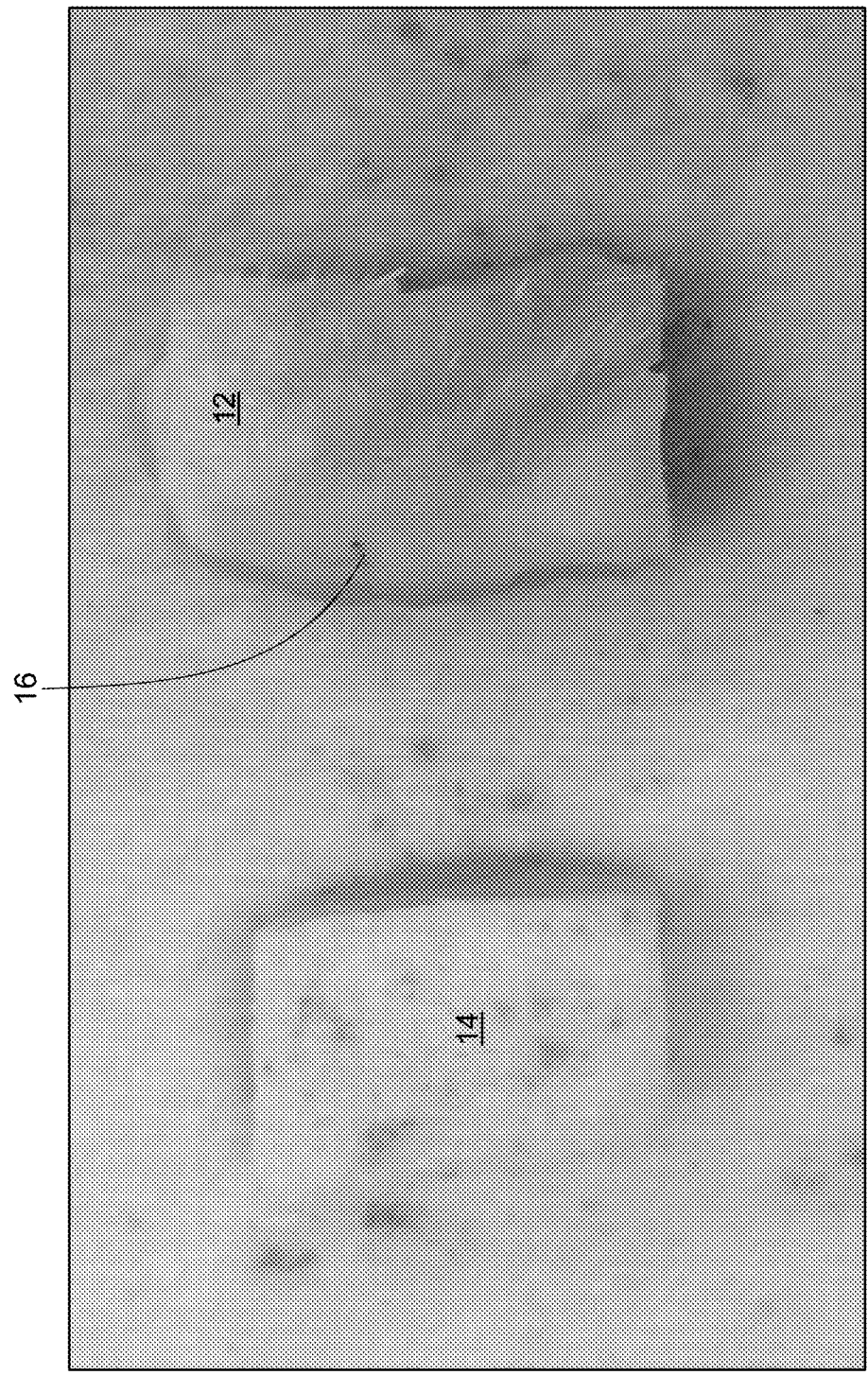
FIG. 1E is close up photograph of the two regions of the skin illustrated in FIG. 1D.

Referring to FIG. 1C, a close-up photograph of the skin surface having a wounded portion 12 and the uninjured portion 14 is shown. Wounded portion 12 comprises a first wound 12a and a second wound 12b, each made with a scalpel. By visual inspection, it is apparent that no damage to the uninjured portion of the skin occurred as a result of the application of the device to the skin and its subsequent generation of heat in situ. It is also apparent that the injured portion of the skin 12 was cauterized as a result of the heat generated in situ by the exothermic reaction between the sodium metal in the heat-generating component of the device and water present at the site of contact on the skin. Referring to FIG. 1D, the injured area of the skin 12 was removed after treatment with the device and a portion of the uninjured portion of the skin 14 was also removed after treatment for further inspection. Referring to FIG. 1E, a magnified view of both portions of the skin 12, 14 is shown. In this view, superficial blood vessels, such as that identified as 16, in the injured portion of the skin 12 were not affected by the heat generated upon application of the device and its sodium metal heat-generating component to the surface of the skin. Accordingly, the effect of the heat resulting from the exothermic reaction of the sodium metal in the device and water at the site of contact appears visually to be purely superficial on the outer layer of the wounded skin 12. The skin wound was closed or cauterized by application of the device, to aid and/or initiate the wound healing process.

Figure 1F:
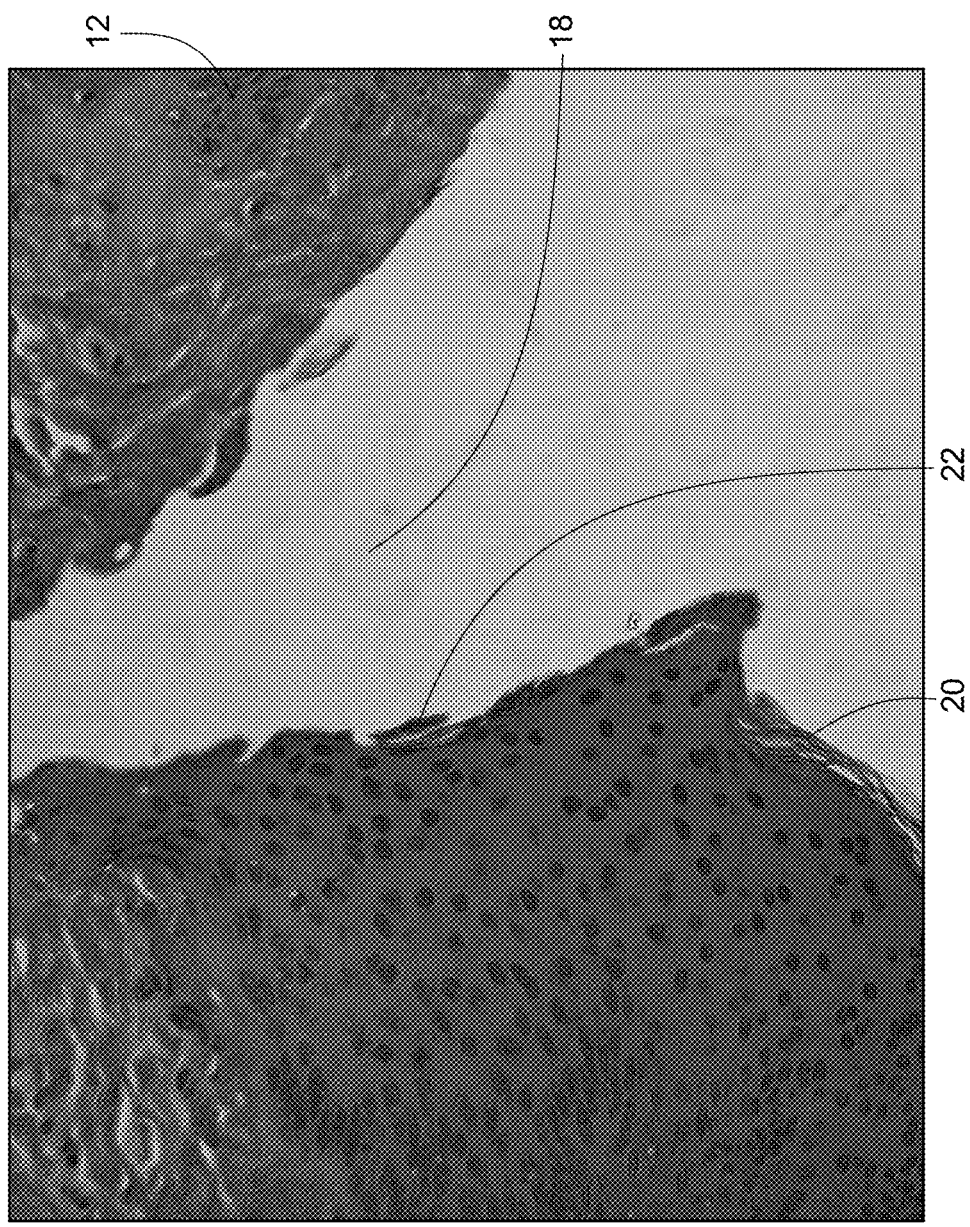
FIGS. 1F-1G are photomicrographs of cross sections of the top surface portion of the first wound (FIG. 1F) and a second wound (FIG. 1G) in the skin of FIGS. 1C-1E.
Figure 1G:
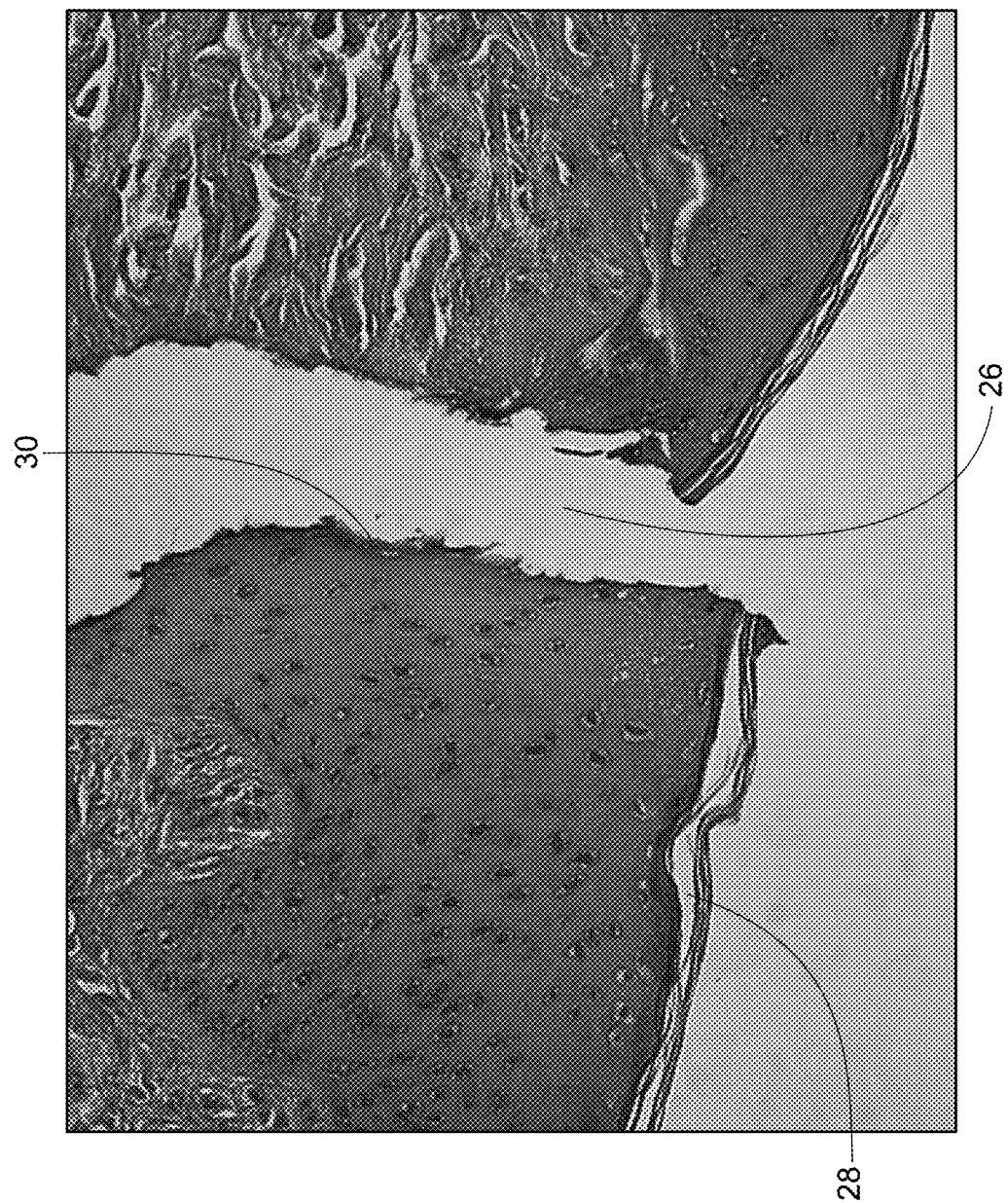
Figure 1H:
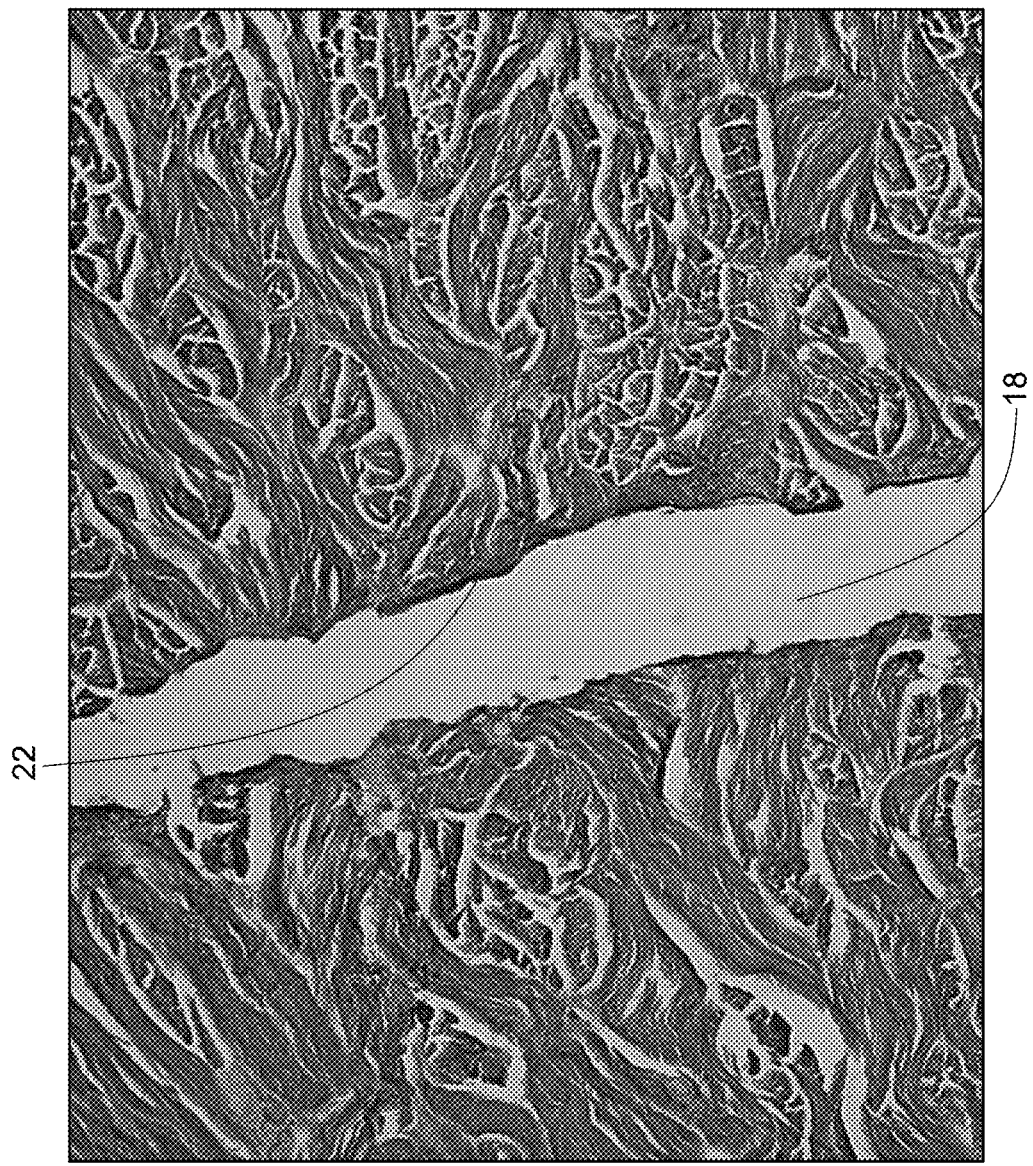
FIG. 1H is a photomicrograph of a cross section of a lower portion of the wound in the skin illustrated in FIGS. 1C-1E.

Cross sectional views of the injured region of the skin and the uninjured (control) region of the skin were taken. Referring to FIG. 1F, a photomicrograph of a cross section of a wound in the injured portion of the skin 12 is shown. As seen, incision 18 extends through the stratum corneum 20 and the upper layers of the skin. The skin adjacent the incision 18, e.g. the stratum corneum identified as the numerical identifier 20 in the photograph, was unaffected by the heat generated in situ upon application of the device to the wounded region. Skin within the incision 18 reveals that a layer 22 approximately two cells deep has been cauterized. This result was not expected, as it indicates that the sodium metal reacted quickly with water in the exposed tissues, and that the reaction stopped once the water had been consumed. This result is in contrast with conventional methods of cauterization which damage skin tissues much more deeply. With reference now to FIG. 1H, a photomicrograph further down incision 18 is shown. The dermis of the skin shows that a cauterized layer 24 is still very thin relative to the surrounding tissue, which was also unexpected. FIG. 1G shows a second incision 26 of wound 12 (different from the incision shown in FIG. 1F). The photomicrograph confirms the results observed with respect to the incision 18 of FIG. 1F—that the outer surface 28 of the skin, including the stratum corneum, was unaffected by the heat generated upon application of the device and its heat generating component comprising sodium metal, and that a layer 30 approximately two cells deep was sealed or cauterized as a result of the heat released by the exothermic reaction between water in the wounded tissue and the sodium metal in the heat-generating component.

Figure 1I:
FIGS. 1I-1J are photomicrographs of cross sections of two different regions of the top surface of the uninjured portion of the skin illustrated in FIGS. 1C-1E.
Figure 1J:

Referring to FIG. 1I, a photomicrograph of a cross section of the uninjured skin region 14 is shown. By inspection, it is apparent that the appearance of the uninjured skin is entirely normal through all of the layers of the skin. This result indicates that the uninjured skin, not having much if any water available for reaction with the sodium metal in the heat-generating component of the device when it was applied to the uninjured skin site, did not generate heat by an in situ reaction with the sodium metal during the time the bandage-like device was applied to the skin surface. FIG. 1J, which is a photomicrograph of another cross section of the uninjured skin 14, confirms the result observed in FIG. 1I, that the layers of the uninjured skin were unaffected by contact with the device, and that a lack of water at the site of contact limited the exothermic reaction with the sodium metal in the device.

From the study described in Example 1 and the drawings in FIGS. 1A-1J, it can be appreciated that upon application of the device to a surface, the amount of heat generated is controlled by, limited by, or proportional to the amount of alkali metal and/or the amount of water at the surface that is available for reaction with the alkali metal.

Another embodiment of a device and use thereof is detailed in Example 2. In this embodiment, a device designed to render a surface substantially aseptic is contemplated. As a model for a surface to be treated, petri dishes filled with lysogeny broth were streaked with *Escherichia coli* (*E. coli*). One of the petri dishes was designated to be a control or reference, and was not further treated during the study. A second petri dish was treated with water. A third petri dish was treated with a water and sodium metal for about 10 seconds. Photographs of the petri dishes were taken a time points of 0 hours (i.e., at the time of treatment) and at 4 hours, 24 hours and 48 hours post-treatment to observe growth of the *E. coli* population. Results are shown in FIGS. 2A-2L.

Figure 2C:
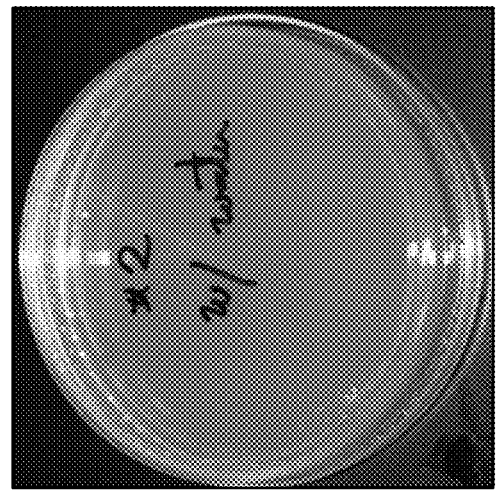
FIGS. 2A-2C are photographs of petri dish streaked with *Escherichia coli* bacteria, the photograph taken immediately after streaking (at an elapsed time equal to 0 hours), where the petri dishes are labelled according to treatment to be applied: 'reference' (control, untreated (FIG. 2A)), "water" (FIG. 2B) and "water+device" (FIG. 2C)
Figure 2B:
Figure 2A:
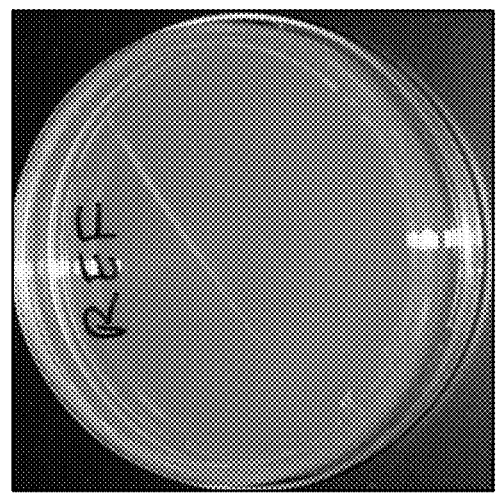
Figure 2F:
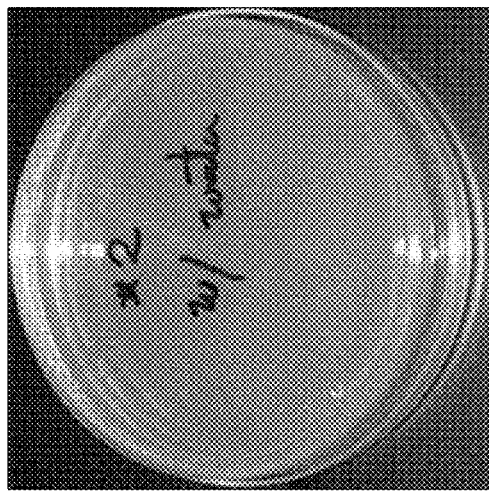
FIGS. 2D-2F are photographs of the petri dishes 4 hours after streaking with *E. coli* and untreated (FIG. 2D), treated with water only (FIG. 2E) and treated with water and a device as described herein (FIG. 2E)
Figure 2E:
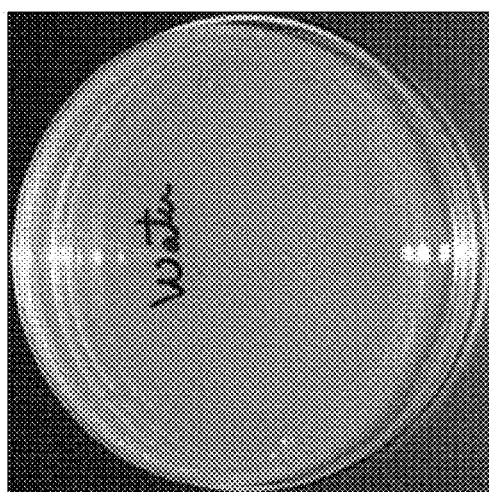
Figure 2D:
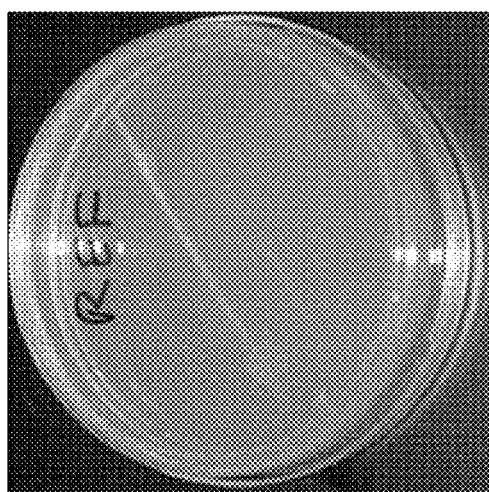
Figure 2I:
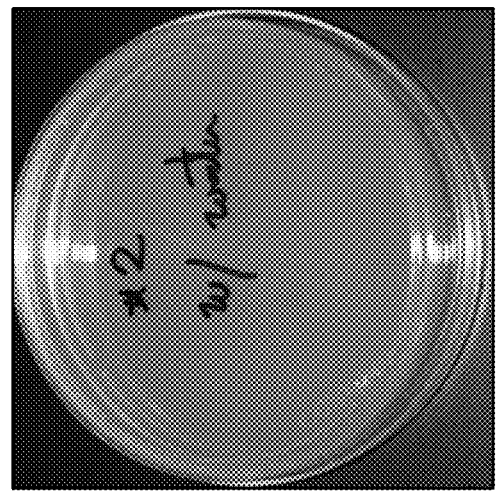
FIGS. 2G-2I are photographs of the petri dishes 24 hours after streaking with *Escherichia coli* bacteria and not treated (reference, FIG. 2G), treated with water (FIG. 2H), and treated with a device as described herein (FIG. 2H)
Figure 2H:
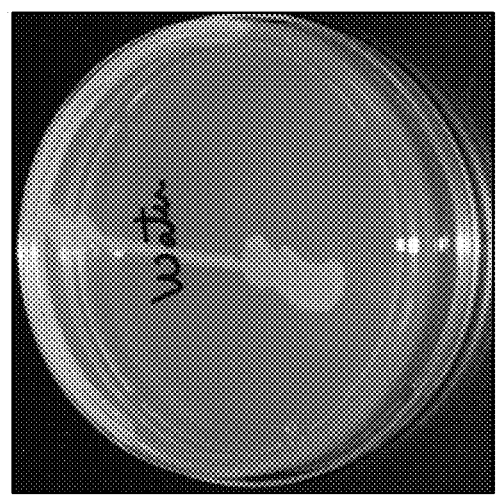
Figure 2G:
Figure 2L:
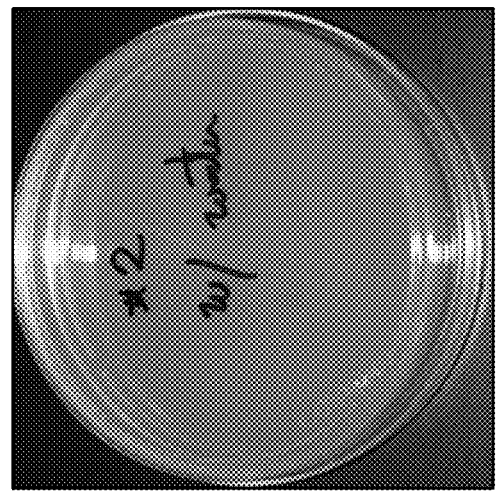
FIGS. 2J-2L are photographs of the petri dishes 48 hours after being streaked with *Escherichia coli* bacteria and not treated (reference, FIG. 2J), treated with water (FIG. 2K), and treated with a device as described herein (FIG. 2L)
Figure 2K:
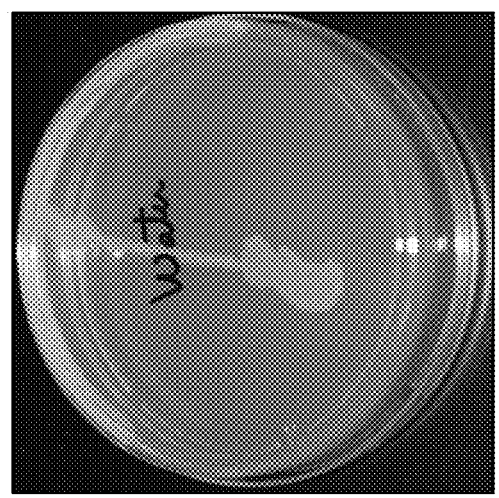
Figure 2J:

Referring to FIGS. 2A-2C, the dish shown in FIG. 2A was the reference dish, the dish in FIG. 2B was actively washed with sterile water, and the dish in FIG. 2C was contacted with sodium metal particles for less than 10 seconds after actively washing with sterile water. FIGS. 2A-2C show the appearance of the *E. coli* streaks as originally applied to each dish following introduction of the water and water/sodium metal mixture (time=0 hours). The dishes 4 hours after treatment are shown in FIGS. 2D-2F, where the dish in FIG. 2D was the reference dish, FIG. 2E was the water treated dish, and FIG. 2F was the water/sodium metal treated dish. Some growth of *E. coli* in the reference dish (FIG. 2D) can be seen at this time point (4 hours). The dishes 24 hours after treatment are shown in FIGS. 2G-2I, where the dish FIG. 2G was the reference dish, FIG. 2H shows the water treated dish, and FIG. 2I shows the sodium metal/water treated dish. Significant *E. coli* growth can be seen in the reference and water treated dishes, but no bacterial growth was observable in the sodium/water treated dish. The dishes 48 hours after treatment are shown in FIGS. 2J-2L, where the dish FIG. 2J was the reference dish, FIG. 2K shows the water treated dish, and FIG. 2L shows the sodium metal/water treated dish. As can be observed, both the reference and water treated dishes experienced significant growth of the *E. coli* bacteria, while no bacterial growth was observed in the sodium metal/water treated dish. This result indicates that the heat generated in situ from the exothermic reaction between the sodium metal and the water present at the treatment surface can be used to render the infected surface substantially aseptic. Accordingly, in one embodiment, a device is provided that is comprised of a heat-generating component having an alkali metal carried on a substrate. The alkali metal is present in an amount sufficient to react exothermically with water at the site of contact on a surface to be treated to generate heat. The heat is generated in an amount sufficient to raise the temperature of the site of contact and, in some cases depending on the thermal properties of the surface, a peripheral zone about the site of contact. The rise in temperature at the site of contact, and optional peripheral zone, is sufficient to achieve an intended effect, such as destruction of a pathogen at the site or alteration of a condition of a tissue.

Figure 3B:
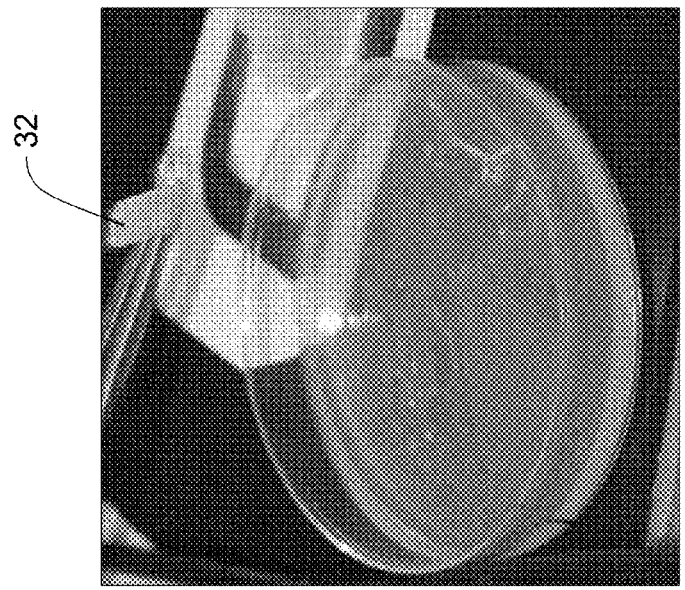
FIG. 3B is a photograph of the petri dish of FIG. 3A following application of sodium metal to the surface of the petri dish.
Figure 3A:
FIG. 3A is a photograph of a petri dish containing a growth of bacteria thereon.

In another study, described in Example 3, a device for rendering a surface aseptic was evaluated. In this study, the infected surface was modeled by a petri dish with a plurality of *E. coli* bacterial colonies. The petri dish is shown in FIG. 3A. A device having a heat-generating component comprised of a substrate and sodium metal (like that described in Example 1) was applied to a portion of the surface of the dish to define a point of contact. No exogenous water was applied to the surface to be treated with the device, as bacteria retain a coating which tends to bind water inherently thereto. FIG. 3B shows the dish following contact with the heat-generating component 32 of the device to the bacteria-infected surface at a point of contact. As can be observed from the visual appearance of the *E. coli* bacterial colonies after treatment (dish in FIG. 3B), heat generated in situ upon application of the device and its heat-generating component comprising sodium metal reacted with water present in situ at the point of contact (i.e., water in the bacterial colonies). The heat raised the temperature at the site of contact to a temperature sufficient to destroy the bacteria. This study illustrates that the devices contemplated herein that comprise a heat-generating component comprising an alkali metal generate heat in situ by an exothermic reaction with water present at the point of contact at the surface to be treated, and that the heat generated is sufficient to raise the temperature of the treatment zone to a temperature sufficient to render it the treatment zone substantially aseptic. Reference to 'treatment zone' intends the point of contact and a zone adjacent the point of contact that is heated to a temperature sufficient to achieve the desired effect (e.g., destroying a pathogen or altering a state of a tissue).

Figure 4A:
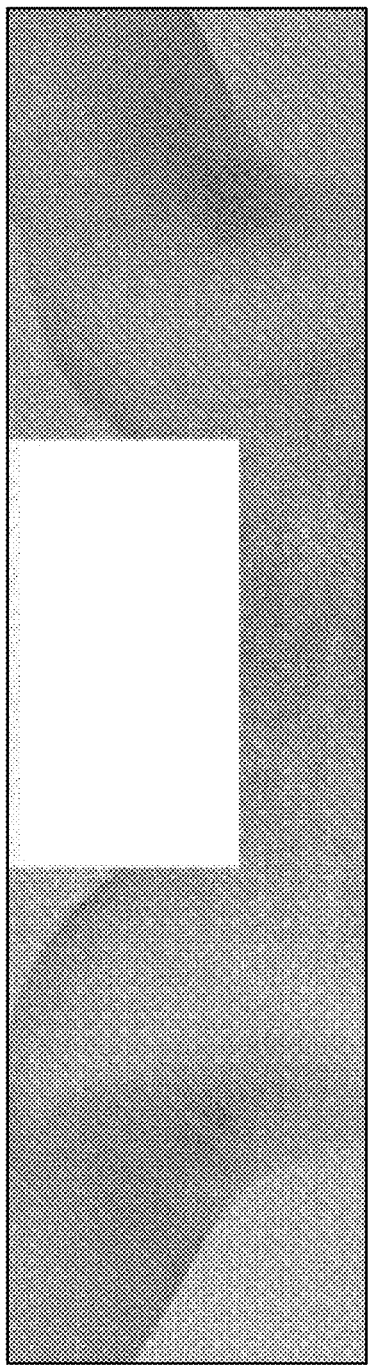
FIG. 4A is a photograph of a male patient with hyperhidrosis treated for stain testing at time equal 0 minutes.
Figure 4B:
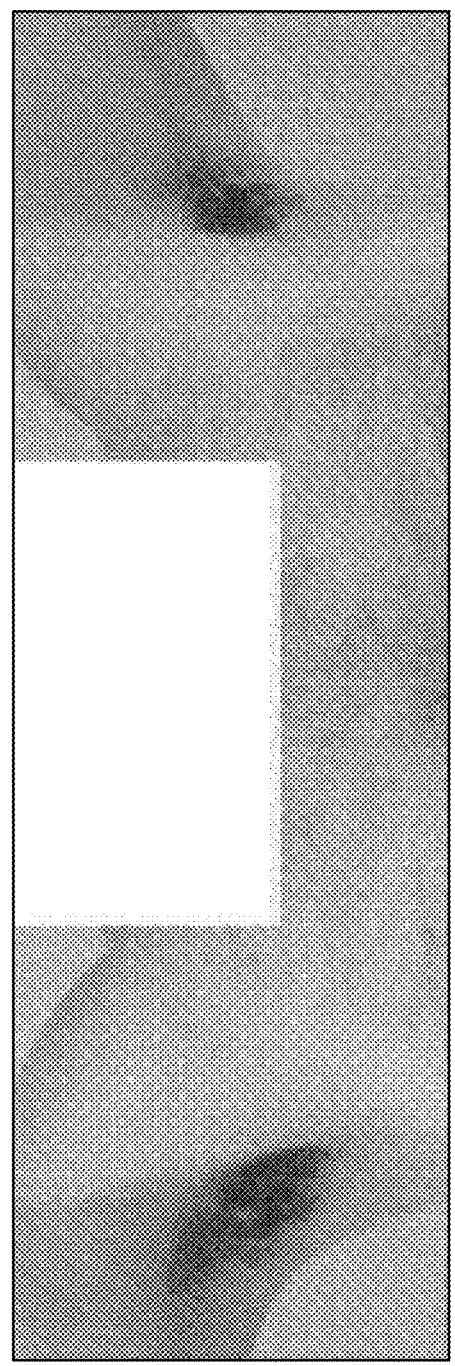
FIG. 4B is a photograph of the same male patient at time equal 5 minutes.

In another embodiment, devices are constructed for generation of heat for the purpose of attenuating or reducing on a temporary or permanent basis excessive sweating. Devices constructed for this application are described with reference to Examples 4-6. In a first exemplary device, a heat-generating component was modeled by a mixture of a NaK alloy admixed with an anhydrous aluminum salt. The heat-generating component was applied to shaved axilla of a subject suffering from excessive sweating (Example 4). Before application of the heat-generating component, the shaved axilla were stain tested to visualize sweat production. In the stain test, iodine solution was applied to the shaved axilla, the iodine-treated area was dried, and then the iodine-treated, dried area was dusted with starch. When sweat is excreted in the axilla regions, a reaction between the iodine and the starch in the presence of the sweat occurs and turns the iodine-treated area black in color. Photographs of the axilla before treatment with the heat-generating component are shown in FIGS. 4A-4B. FIG. 4A shows the left and right axilla of the male patient taken immediately after dusting with starch and the photograph in FIG. 4B shows the left and right axillar of the same patient 5 minutes later. The presence of the black color indicates the severity of the hyperhidrosis present in this patient and that most of the axilla skin is participating in creating hyperhidrosis in this patient.

The heat generating mixture of the NaK alloy admixed with anhydrous aluminum salt was applied directly to the axilla regions for a treatment period of about 10 minutes. Following application of the heat-generating mixture to the axilla, the axilla regions were stain tested. Photographs of the regions were taken at time equal 0 minutes corresponding to immediately prior to stain test treatment and at 5 minutes post stain test treatment and at 10 minutes post stain test treatment, while the heat-generating mixture was still present in the axilla regions. The photographs are shown in FIGS. 4C-4E.

Figure 4C:
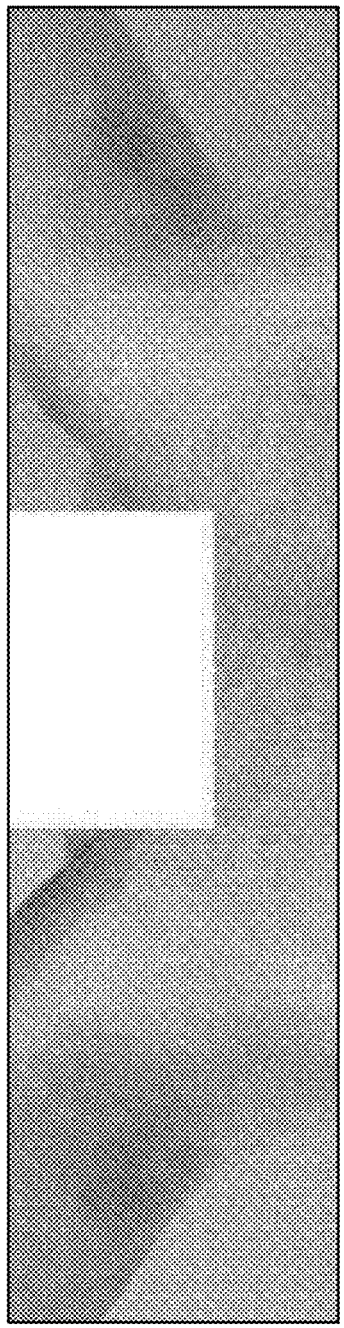
FIG. 4C is a photograph of the male patient of FIG. 4A following a single treatment with NaK in an aluminum salt base and treated for stain testing at time equal 0 minutes.
Figure 4D:
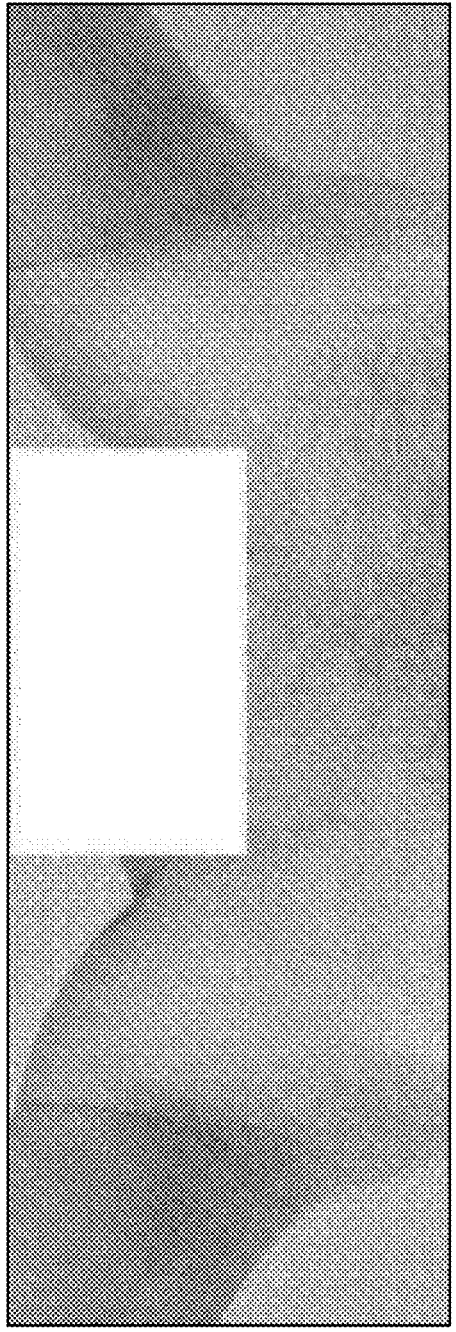
FIG. 4D is a photograph of the male patient of FIG. 4A at time equal 5 minutes post treatment.
Figure 4E:
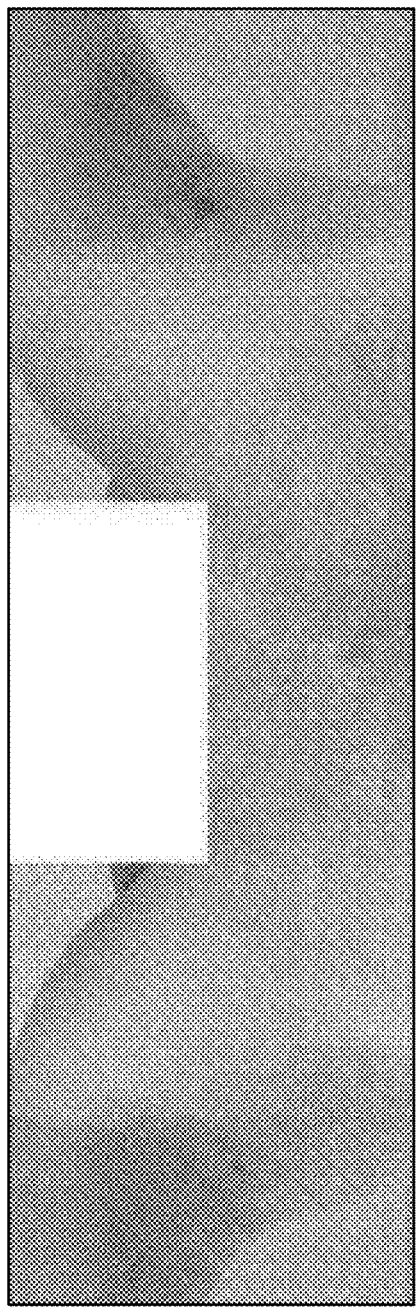
FIG. 4E is a photograph of the patient of FIG. 4A at time equal 10 minutes post treatment.

The photograph in FIG. 4C shows the left and right axilla following treatment by applying liquid NaK in an anhydrous aluminum salt base directly to the skin for a treatment period (10 minutes). The photograph in FIG. 4C was taken at time equal 0 minutes immediately prior to stain test treatment. The photograph in FIG. 4D shows the axilla of the patient at 5 minutes post stain test treatment while the NaK solution is still applied, and FIG. 4E shows the axilla of the patient at time equal 10 minutes post stain test treatment at the conclusion of the NaK application period. When compared with the baseline data in FIG. 4B marked improvement is observed after a single treatment of the heat-generating component. That is, a marked reduction in sweat production occurred. During the treatment period, the NaK alloy entered the sweat ducts and/or the sweat glands and reacted with water present in the ducts and/or glands as it was being produced (released) by the patient. The alloy and water in the sweat react in situ in an exothermic reaction to generate heat. Without being bound by any theory, it appears that the heat generated by the reaction raises the temperature at the treatment site to a temperature sufficient to ablate the ducts and/or glands, causing their destruction and preventing them from operating to produce the excess amounts of sweat consistent with hyperhidrosis. Because of the ablation of the sweat ducts and/or glands, a permanent reduction of the axillary skin's ability to excrete sweat may be achieved, as the ablation may be permanent, as the skin tissue may not regenerate the ablated ducts and/or sweat glands.

Figure 5C:
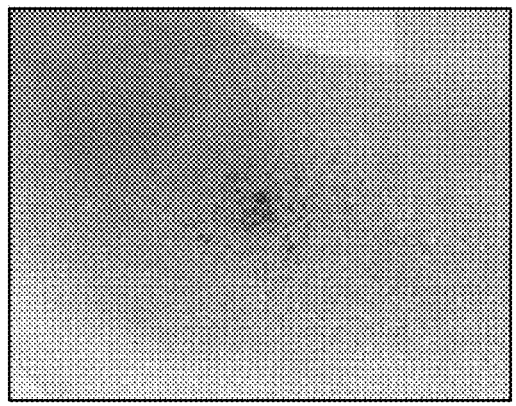
FIG. 5C is a photograph of the left axillia of the patient of FIG. 5A after a second treatment with an oil emulsion including NaK at 90 seconds post treatment for stain testing.
Figure 5B:
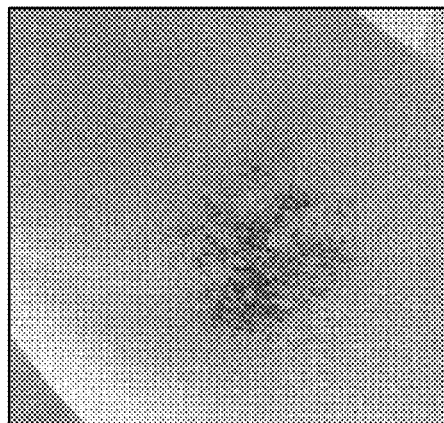
FIG. 5B is a photograph of the left axillia of the patient of FIG. 5A after treatment by an oil emulsion including NaK at 90 seconds post treatment for stain testing.

In another study, a composition of an alkali metal admixed with other ingredients suitable for forming a skin-safe heat-generating composition for application to the skin was prepared. The purpose of this study was to illustrate that the alkali metal, e.g., sodium metal, potassium metal, or sodium and potassium metal alloy, may be incorporated with other ingredients to form a final composition for application to a subject. These additional ingredients may be actives or inactives selected to perform a variety of compositional or therapeutic effects. In this study, a composition comprised of NaK and pure mineral oil was prepared, where the ratio of the components was 1 part of NaK to 20 parts of mineral oil (1:20) by volume. As described in Example 5, the composition was applied to the left axilla of a patient diagnosed with hyperhidrosis and allowed to remain for 5 minutes before being removed. The left axilla was stain tested to visualize sweat production, and photographs of the left axilla of the patient were taken at the following time points: after stain testing for 90 seconds prior to treatment with the NaK/mineral oil solution (FIG. 5A), following treatment with the NaK/mineral oil solution after stain testing for 90 seconds (FIG. 5B). Treatment with the NaK/oil mixture was repeated for 5 minutes and the area when then stain tested. A photograph of the region was taken 90 seconds after stain testing (FIG. 5C).

Figure 5A:
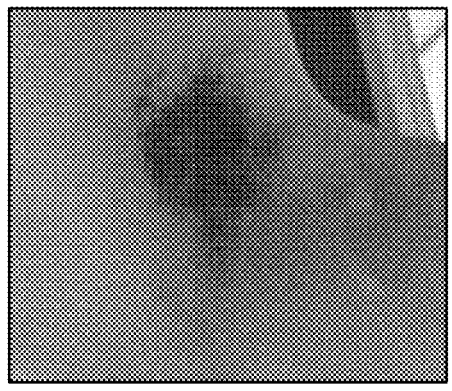
FIG. 5A is a photograph of a patient's left axilla treated for stain testing at 90 seconds post testing prior to treatment.

FIG. 5A shows the left axilla of the patient after stain testing for 90 seconds prior to treatment with the NaK/mineral oil solution. FIG. 5B shows the left axilla of the same patient following treatment with the NaK/mineral oil solution as previously described after stain testing for 90 seconds. FIG. 5B indicates marked improvement over the baseline testing shown in FIG. 5A. To see if additional improvement could be obtained, the treatment with the NaK/mineral oil solution was again repeated for 5 minutes and stain testing for 90 seconds was undertaken. FIG. 5C is a photomicrograph of the twice-treated area 90 seconds after stain testing. Additional marked improvement is noted, as evidenced by a further reduction in sweat production (reduction in black color produced in the treatment region). At a glandular level, of the effect of the heat generated in situ and concomitant temperature increase may be temporary or permanent depending on the extent of ablation of the tissues.

A wide variety of alkali metal/mineral oil ratios may be employed in various implementations, including about 1:1 to about 1:1000. Other active and inactive ingredients that could be employed with alkali metal/mineral oil compositions include any anhydrous base materials including anhydrous synthetic polymers and mixtures of anhydrous base materials and anhydrous synthetic polymers.

In other embodiments, the alkali metal may be mixed with an aluminum salt, magnesium salt, or a combination of both. An example of this embodiment is detailed in another study described in Example 6. In this study, a device with a heat-generating component in the form of a mixture of NaK and an aluminum salt-containing base was prepared. The heat-generating component was in the form of semi-solid, like an antiperspirant semi-solid. The heat-generating component contained 1 part of NaK to 100 parts of antiperspirant containing the aluminum salt (1:100) by volume. The heat-generating component was applied topically to the right axilla of a patient diagnosed with hyperhidrosis and allowed to stand for 5 minutes prior to being removed. The right axilla was then stain tested as set forth in Example 4. Photographs of the right axilla prior to treatment with the NaK/antiperspirant composition after 90 seconds have elapsed during a stain test (FIG. 6A) and following treatment with the NaK/antiperspirant composition after 90 seconds had elapsed during a stain test (FIG. 6B) were taken.

FIG. 6A shows the right axilla prior to treatment with the NaK/antiperspirant composition and 90 seconds after a stain test. FIG. 6B shows the right axilla following treatment with the NaK/antiperspirant composition and 90 seconds after a stain test. This study indicates that a substantial reduction in sweat product is achieved after a single treatment of the heat-generating device, and that two, three, four, five, or more treatments may be used to achieve further reduction in sweat production via ablation of the sweat ducts and/or sweat glands or other structures in the skin being treated.

Alkali metal/antiperspirant compositions may include any of a wide variety of ratios of alkali metal to aluminum salt-containing compositions. Example of such ratios include about 100:1 to about 1:1000. Other active and inactive ingredients that could be employed with alkali metal compositions include anhydrous polymers or mixtures of anhydrous polymers, and some examples of suitable ingredients are itemized in the table of Example 6. Those of ordinary skill will readily be able to select various active and inactive ingredients using the principles disclosed herein.

Contemplated is a kit that comprises a device as described herein in combination with instructions for use, and, optionally, a wipe comprising a solvent for cleansing the site of contact to which the device is intended to be applied. In one embodiment, the wipe is a gauze pad and in one embodiment the solvent is isopropyl alcohol.

II. METHODS OF USE

The heat-generating devices described herein can be used for a variety of purposes, and several are now described.

A. Rendering a Surface Substantially Aseptic

In a first aspect, a method for rendering surfaces substantially aseptic is contemplated. The surfaces intended for use in this method encompass any surface on which a pathogen or undesirable species resides or grows, including skin surfaces, counter top or bench top surfaces, or surgical instrument surfaces. With respect to skin surfaces, the topical skin treatment of pathogens on the skin or that involve moisture secretion by the skin include, by way of non-limiting example, acne, fungal infections, removal of warts (applied before or after removal of the wart), cold sores (Herpes simplex), and any other pathogen that can be killed or denatured through application of heat.

Various device implementations that contain sodium metal and/or NaK may be developed for use to create or render a surface substantially aseptic. In these implementations, the device comprises a heat-generating component as described above and an applicator that is shaped/designed so that a user can contact the heat-generating component with the surface in such a manner to render it substantially aseptic. For example, where the surface to be rendered aseptic is skin, the user may first apply an amount of water to the skin to moisten it or hydrate the area to be treated. In most cases, addition of exogenous water to the treatment size is not required. Holding the applicator, the user brings the heat-generating of the device into contact with the skin at the site to be treated, thereby generating heat during reaction of the sodium metal with the water on the skin. In one embodiment, the device is held stationary at the treatment site, until an indicator light on the device indicates that the temperature at the point of contact has decreased to a preselected temperature, or has decreased from its measured maximum temperature during treatment by a certain percentage. In various implementations, such as in the holder implementations, the alkali metal is included in the applicator in a retractable fashion. In other embodiments, the alkali metal of the heat generating component is on an outer surface of the applicator.

In other embodiments, the base or substrate is a container that holds a quantity of dry alkali metal therein and which is designed to allow the user to contact their hands with the powdered alkali metal. In such implementations, the container could be, by non-limiting example, a pouch, a dish, a box, a bag, a reclosable bag, or any other structure capable of holding dry alkali metal and providing access to a user. As the user contacts the powdered alkali metal with their skin, the dry alkali metal and in situ water undergo an exothermic reaction to generate heat. The heat is generated in an amount that will, for example, cauterize any wound on the user's hand. Also, the exothermic reaction may create, in addition to heat, an alkali metal hydroxide, such as sodium hydroxide or potassium hydroxide. The heat and/or alkali hydroxide kills and/or denatures pathogens on the surface to be treated (e.g., in this embodiment, a user's hands). Thus, in some embodiments, the device can simultaneously cauterize and render a surface substantially aseptic.

The applicator may be a needle, wipe or sponge. In these embodiments, the device can render an area within a patient or other area within another structure aseptic. It may also aid in performing injection lipolysis through the alkali metal reacting with water in situ, e.g., water stored in fat tissue adjacent to the location where the needle is inserted. In such implementations, the needle may be hypodermic and hollow. In other implementations, the needle may not be hollow and the alkali metal is present as a coating on the needle.

In other embodiments, the device is intended for use in sterilizing instruments. In this embodiment, the base or substrate can be a structure designed to hold one or more instruments for sterilization and the alkali metal is present at a suitable location. Instruments placed into the base are sterilized when the alkali metal undergoes its exothermic reaction with water present on the instruments, and the reaction generates an amount of heat sufficient to sterilize the surface of the instruments. In other embodiments, the device is designed to contact the alkali metal with a surface of an instrument to render its surface sterile, where the instrument may be pre-wetted with water or may have residual water present from rinsing after use.

In the methods of use described herein, various approaches and structures may be used to prevent or minimize contact between the ambient air and the alkali metal before the device is ready to be used. Such approaches and structures gas impermeable packaging, nitrogen or other inert gas purging systems that keep oxygen from contact with the heat-generating component of the device while not in operation.

B. Wound Closure

In another embodiment, devices described herein are used for closure of a wound, by cauterizing the wound as a result of the temperature increase at a site of contact, and a surrounding peripheral area to form a treatment zone, by heat generated by the exothermic reaction between the alkali metal of the device and water present at the site of contact. Cauterization of a wound closes the wound, to aid in and/or accelerate the wound healing process. Cauterization may be employed in various situations where wounds are formed, such as surgical procedures, wart removal, cryogenic therapies, battle wounds, extreme sports injuries in remote locations, and many other situations where the water from the blood and tissue in the wounds can be reacted with the alkali metal to cauterize the wound.

As discussed above, heat and the concomitant temperature increase achieved during use of the device is also sufficient to render a surface at the point of contact (and surrounding treatment zone) aseptic. Accordingly, a method of simultaneously cauterizing a wound for healing and rendering a surface substantially aseptic is contemplated. For example, in a laboratory situation where pathogens are being handled and where the researcher wishes to ensure the skin surface of the hands is intact, the researcher may lightly moisten her hands and then apply powdered sodium metal or NaK, permitting any open wounds on the hands to be closed and her hands to be rendered aseptic. After handing the pathogens, the researcher may repeat the process, and ensure that her hands are substantially free from the pathogens. Other situations involve battlefield injuries where wounds need to be stabilized before treatment in a hospital or in a battlefield hospital where a surgeon does not have access to any or a reliable source of electricity to permit other hand or wound sterilization systems to be employed. A wide variety of potential use situations and structures are possible using the principles disclosed herein. In medical applications, the ability to cauterize and/or render a surface aseptic on contact may be useful or critical depending upon the conditions. For example, on a battlefield, there may be no electricity or water present, and the need to stop bleeding and stop infection while waiting to get an injured soldier to medical attention may be critical.

C. Excessive Sweating: Hyperhidrosis and Perceived Excessive Sweating

Hyperhidrosis is a medical condition characterized by excessive sweating in the armpits (axillae), palms, soles of the feet, face, scalp, and/or torso. Hyperhidrosis when not secondary to a known underlying medical condition is referred to as primary focal hyperhidrosis. Primary focal hyperhidrosis is defined as excessive, bilateral, and relatively symmetric sweating occurring in at least one of the following sites: the axillae, palms, soles, or craniofacial region (Hornberger, J. et al., *J. Am. Acad. Dermatol.*, 51:274-86 (2004)). Criteria recommended for establishing the diagnosis of primary focal hyperhidrosis include (1) focal, visible, excessive sweating of at least 6 months duration without apparent cause with at least two of the following characteristics: (i) bilateral and relatively symmetric; (ii) impairs daily activities, (iii) frequency of at least one episode per week; (iii) age of onset less than 25 years; (iv) positive family history; and (v) cessation of focal sweating during sleep (Id). In subjects that report excessive sweating yet a medical diagnosis of primary focal hyperhidrosis is not satisfied, these subjects have a perceived excessive sweating. The methods of treatment described herein for treating or reducing excessive sweating encompass hyperhidrosis as a medical condition, primary focal hyperhidrosis and secondary hyperhidrosis, as well as perceived excessive sweating.

In this aspect, a method for treating excessive sweating, by reducing temporarily or permanently the amount of sweat produced in each episode of sweating, is provided. The method comprises contacting the skin of the subject at a site of contact where excessive sweating occurs (e.g., axillae, palms, craniofacial region) with a device as described herein. The alkali metal in the heat generating component of the device reacts with water in the sweat at the site of contact to generate heat in situ, where the heat is generated in an amount controlled by or proportional to the amount of water present at the site of contact and where the heat is generated in an amount sufficient to raise the temperature of the point of contact (and preferably a zone around the point of contact) to a temperature that ablates the sweat ducts and/or sweat glands to render them less able to produce sweat.

In one embodiment, a reduction in sweat production is observed for a period of at least 1 day, 2 days, 3 days, 4 days, 5 days, 6 days, 1 week, 2 weeks, 3 weeks or 1 month. The method comprises, in other embodiments, repeating the step of contacting the skin with a device to achieve a further reduction in sweat production or a subsequent reduction in sweat production for a subsequent period of time. The reduction in sweat production is ascertained subjectively, in one embodiment, via a series of questions to the subject, such as those in the classification scales described below (HDDS and HHIQ). In another embodiment, the reduction in sweat production is ascertained objectively, such as gravimetrically or via an iodine test. In gravimetric measurements, a piece of filter paper is weighed and is then applied to the palm or axilla (or other body region) for a period of time measured with a stopwatch. The paper is then weighted and the rate of sweat production is calculated in mg/min. In one embodiment, the method is effective to achieve at least a 25% reduction in sweat production, more preferably at least a 50% reduction in sweat production, for a period of 3 days, 5 days or 1 week.

In one embodiment, the method is used for reduction of excessive sweating in a patient experiencing moderate to severe excessive sweating. Classification of hyperhidrosis as mild, moderate or severe is, in one embodiment, made using the Hyperhidrosis Disease Severity Scale (HDDS). The HDDS is a four-point scale designed to assess the severity of hyperhidrosis in clinical practice and to assess the effectiveness of hyperhidrosis treatment. The scale can be administered by a clinician or by the patient, and asks the patient to choose from the following four statements the one that best applies:
1. My sweating is never noticeable and never interferes with my daily activities.
2. My sweating is tolerable but sometimes interferes with my daily activities.
3. My sweating is barely tolerable and frequently interferes with my daily activities.
4. My sweating is intolerable and always interferes with my daily activities.

Selection of 3 or 4 indicates severe hyperhidrosis and selection of 2 indicates moderate hyperhidrosis, and a selection of 1 indicates mild hyperhidrosis. Other measures of hyperhidrosis include the Hyperhidrosis Impact Questionnaire® (HHIQ), gravimetric sweat production, and dermatology quality of life index (DLQI). The validity and reliability of the HHIQ scale, and its utility in measuring the burden of the disease and its effect in patients, is documented in the literature, for example, by Teale et al., *Qual Life Res.*, 11:702 (2002); Naumann et al., *Br. J Dermatol*, 147:1218 (2002); and Strutton et al., *J. Am Acad Dermatol*, 51:241 (2004).

D. Treatment of Symptoms Associated with Allergies

In another embodiment, a method for ameliorating or treating symptoms associated with allergies is provided. A common symptom of allergies, especially seasonal allergies, is a runny nose. Use of the device described herein to reduce or substantially reduce nasal discharge or other symptoms of seasonal allergies is contemplated, by contacting the device to a location on a patient with excessive water-related swelling or discharge. Upon contact, the alkali metal in the heat generating component of the device reacts with water in the discharge at the site of contact to generate heat in situ, where the heat is generated in an amount controlled by or proportional to the amount of water present at the site of contact and where the heat is generated in an amount sufficient to raise the temperature of the point of contact (and preferably a zone around the point of contact) to a temperature that ablates the tissue region, rendering it less able to produce discharge. In one embodiment, the method is used to treat symptoms of sinusitis, where the sinusitis is associated with either an infectious or an inflammatory standpoint, thus allowing the symptoms and signs of sinusitis to be alleviated. Any of the various devices disclosed herein can be used in this method, including pastes and nasal swabs to apply the alkali metal to the treatment site.

E. Ablation of Tissue

In another embodiment, a method for ablating tissue with the devices described herein is contemplated. For example, the devices may be used to reduce or substantially reduce the tumor mass of a cancer or enlarged organ following at least one application of the device to the affected location. Any of the various devices disclosed herein may be used. In particular implementations, infusion catheters, needles, and cannulas may be utilized to transport the heat-generating component to the treatment site.

The devices may also be used to reduce or substantially reduce adipose tissue volume following at least one application of the heat-generating component to a location on a patient containing an undesirable amount of or shape of fat tissue. Any of the various devices disclosed herein may be used. In particular implementations, infusion catheters, needles, and cannulas may be utilized to transport the heat-generating component to the treatment site. Particular areas which may be treated include submental fat, breast tissue (to aid in breast lifting/reducing), thighs, buttocks, hips, cheeks, the neck, and other areas which contain adipose tissue and/or fat to be reduced/altered.

III. EXAMPLES

The following examples are illustrative in nature and are in no way intended to be limiting.

Example 1

Device in the Form of a Bandage for Wound Closure

A device was prepared using a sterile gauze pad as a substrate. Sodium metal was mixed into petroleum jelly to form a paste, which was then applied to one side of the substrate. The opposing side of the substrate was overlayed with a backing member having a peripheral adhesive to form a bandage-like device (see FIG. 1A).

A section of viable porcine skin was obtained, and a wound was made using a scalpel. The device was applied to the porcine skin so that the substrate with sodium meal was in contact with the wound and with adjacent uninjured, intact skin, the latter site of contact serving as a control. The device was left in place for 15 seconds and removed. The appearance and micrographic appearance of both the uninjured skin tissue and the wounded tissue was observed. Results are shown in FIGS. 1C-1J.

Example 2

Streak Testing with *Escherichia coli*

Three petri dishes containing lysogeny broth (LB) were prepared and streaked with a culture of JM109 competent *Escherichia coli* obtained from Sigma-Aldrich of St. Louis, Mo. One petri dish was designated as the reference dish and was untreated. The second dish was actively washed with sterile water after streaking with *E. coli*, and the third dish was contacted with sodium metal particles for less than 10 seconds after actively washing with sterile water. Photographs of the dishes were taken to observe the appearance of the *E. coli* bacterial streaks as originally applied to each dish following introduction of the water and water/sodium metal mixture (time=0 hours, FIGS. 2A-2C) and after incubation under standard growth conditions, at a temperature of 37° C., for 48 hours. The dishes were photographed at 4 hours, 24 hours and at 48 hours, and the results are shown in FIGS. 2D-2F, FIGS. 2G-2I, and FIGS. 2J-2L, respectively.

Example 3

Aseptic Capability of Sodium Metal Through Direct Contacting

A petri dish containing LB broth was cultivated with an *E. coli* bacterial population to create a plurality of colonies distributed across the surface of the dish. After the bacterial colonies were established, a device like that described in Example 1 was applied to the surface of the LB broth and *E. coli* colonies. No additional (exogenous) water was added. The dish was photographed before (FIG. 3A) and after (FIG. 3B) treatment to observe the effect of the heat generated in situ on the bacterial populations.

Example 4

Device for Generation of Heat In Situ

A male patient diagnosed with hyperhidrosis was prepared for treatment with a device by shaving the hair from both axilla. The shaved area was stain tested using an iodine-starch indicator test. Iodine solution was applied to the shaved axilla, the iodine-treated area was dried, and then the iodine-treated, dried area was dusted with starch. A photograph of the axilla of the male patient taken immediately after dusting with starch and at 5 minutes later are shown in FIGS. 4A-4B.

An alkali metal in the form of an alloy of Na and K (hereafter NaK) admixed with an anhydrous aluminum salt was prepared. The mixture was applied directly to the axilla regions for a treatment period of about 10 minutes. Following application of the heat-generating mixture to the axilla, the axilla regions were stain tested, as described in the preceding paragraph. Photographs of the regions were taken at time equal 0 minutes corresponding to immediately prior to stain test treatment and at 5 minutes post stain test treatment and at 10 minutes post stain test treatment, while the heat-generating mixture was still present in the axilla regions. The photographs are shown in FIGS. 4C-4E.

Example 5

Antiperspirant Solution for Generation of Heat In Situ

A composition of NaK and pure mineral oil was prepared at a ratio of 1 part of NaK to 20 parts of mineral oil (1:20) by volume. The resulting mixture was a silvery grey color following sonication for 30 seconds. The composition was then applied to the left axilla of a patient diagnosed with hyperhidrosis and allowed to remain for 5 minutes before being removed. The left axilla was then treated using iodine and starch for stain testing, as described in Example 4. Photographs of the left axilla of the patient were taken: after stain testing for 90 seconds prior to treatment with the NaK/mineral oil solution (FIG. 5A), following treatment with the NaK/mineral oil solution after stain testing for 90 seconds (FIG. 5B). Treatment with the NaK/oil mixture was repeated for 5 minutes and the area when then stain tested. A photograph of the region was taken 90 seconds after stain testing (FIG. 5C).

Example 6

Antiperspirant Device for Generation of Heat In Situ

A mixture of NaK and an aluminum salt-containing composition in the form of a clinical strength antiperspirant formulation marketed under the tradename DEGREE CLINICAL PROTECTION® by Conopco Inc. (Unilever) of London, UK was prepared. The particular components of the antiperspirant formulation are set forth in the table below. The mixture contained 1 part of NaK to 100 parts of antiperspirant containing the aluminum salt (1:100) by volume. The resulting mixture was a whitish solid paste.

The NaK/antiperspirant composition was applied topically to the right axilla of a patient diagnosed with hyperhidrosis and allowed to stand for 5 minutes prior to being removed. The right axilla was then stain tested as set forth in Example 4. Photographs of the right axilla prior to treatment with the NaK/antiperspirant composition after 90 seconds have elapsed during a stain test (FIG. 6A) and following treatment with the NaK/antiperspirant composition after 90 seconds had elapsed during a stain test (FIG. 6B) were taken.

| Ingredient | |
|---|---|
| aluminum zirconium tetrachlorohydrex GLY (aluminum cation) | 20 g in 100 g (20%) |
| NaK | 1 g in 100 g |
| cyclopentasiloxane | (inactive) |
| dimethocone | (inactive) |
| microcrystalline wax | (inactive) |
| C18-C36 acid triglyceride | (inactive) |
| fragrance | (inactive) |
| silica | (inactive) |
| zea mays (corn starch) | (inactive) |
| dimethicone crosspolymer | (inactive) |
| butylated hydroxytoluene (BHT) | (inactive) |

Example 7

Diagnostic Tool for Hyperhidrosis and Treatment Thereof

A female subject concerned with sweating in her axilla and facial area is asked by her clinician to complete the Hyperhidrosis Disease Severity Scale (HDDS), which asks the subject "How would you rate the severity of your hyperhidrosis?" 1. My sweating is never noticeable and never interferes with my daily activities. 2. My sweating is tolerable but sometimes interferes with my daily activities. 3. My sweating is barely tolerable and frequently interferes with my daily activities. 4. My sweating is intolerable and always interferes with my daily activities. The subject is asked to select the statement from choices 1, 2, 3 and 4 that best reflects her experience with sweating of her axilla and face. The subject chooses statement 3, and is assigned a diagnosis of severe hyperhidrosis. The subject is prescribed a device in the form of an antiperspirant stick comprising a sodium-potassium alloy according to Example 6 and applies the composition to her axilla and forehead once per week.

Additional Embodiments of the disclosed device are now recited.

Implementations of devices for cauterizing wounds may include a base and one of sodium metal or a sodium and potassium metal alloy coupled with the base where the base is configured to allow a user to apply the one of the sodium metal or the sodium and potassium metal alloy to an open wound of a patient to cauterize the open wound.

Implementations of devices for cauterizing wounds may include one, all, or any of the following:

The base may be designed to prevent contact of the one of sodium metal or the sodium and potassium metal alloy with one of oxygen or water until just prior to use by a user.

The one of sodium metal or the sodium and potassium metal alloy may be included within a portion of the base.

The base may be a bandage and the one of sodium metal or the sodium and potassium metal alloy may be one of included within and included on a sterile dressing coupled to the bandage.

The one of sodium metal or the sodium and potassium metal alloy may be coupled with the base through being coated on a portion of a surface of the base.

The base may be selected from the group consisting of a dermal roller, a knife, a surgical instrument, a stick, a dermal pen, and a needle.

Implementations of a device for rendering a surface substantially aseptic may include an application and one of sodium metal or a sodium and potassium metal alloy coupled with the applicator where the applicator is configured to allow a user to apply the one of sodium metal or the sodium and potassium metal alloy to the surface to render the surface substantially aseptic.

Implementations of the device may contain one, all, or any of the following:

The applicator may be configured to prevent contact of the one of sodium metal or the sodium and potassium metal alloy with one of oxygen or water until just prior to use by a user.

The one of sodium metal or the sodium and potassium metal alloy may be included within the applicator.

The applicator may be a container adapted to enable the contacting of sodium metal in powdered form with a user's hands to render the user's hands substantially aseptic, cauterize one or more wounds on the user's hands, and/or both render the user's hands substantially aseptic and cauterize one or more wounds on the user's hands.

The applicator may be a needle, a wipe, or a sponge.

The applicator may be a sterilizer which may be configured to mix water with the one of sodium metal or the sodium and potassium metal alloy to generate heat sufficient to render a surface of an item being sterilized sterile.

The applicator may be a sterilizer which may be configured to contact the one of sodium metal or the sodium and potassium metal alloy with a surface of an item to render the surface sterile.

Implementations of a device for rendering a wound substantially aseptic and for cauterizing the wound may include a wound contacting device and one of sodium metal and a sodium and potassium metal alloy coupled with the wound contacting device. The wound contacting device may be configured to allow a user to apply the one of sodium metal and the sodium and potassium metal alloy to the wound to render the wound substantially aseptic and simultaneously cauterize the wound.

Implementations of the device may include one, all, or any of the following:

No external or exogenous water may be used by the wound contacting device.

The wound contacting device may be a bandage including a dressing coupled with the one of sodium metal and the sodium and potassium metal alloy.

The bandage may be configured to, after rendering the wound substantially aseptic and simultaneously cauterizing the wound, ensure that all of the one of sodium metal and the sodium and potassium metal alloy are consumed.

The bandage may be configured to render the wound substantially aseptic and simultaneously cauterize the wound after a passage of a predetermined period of time.

Implementations of a composition for treating hyperhidrosis may include one of sodium metal or a sodium and potassium metal alloy where the one of sodium metal or the sodium and potassium metal alloy is configured to permit a user to apply the one of sodium metal or the sodium and potassium metal alloy to a location of a patient's skin and ablate one of at least one sweat gland or at least one sweat duct in that location.

Implementations of the composition may include one, all, or any of the following:

The composition may include mineral oil.

The mineral oil may be mixed with the sodium and potassium metal alloy in a ratio of 1:20 parts of sodium and potassium metal alloy to parts of mineral oil by volume.

The composition may include a salt-containing composition.

The salt-containing composition may further include aluminum, magnesium, or any combination thereof.

The salt-containing composition may include aluminum and may be mixed with the sodium and potassium metal alloy in a ratio of 1:100 parts of sodium and potassium metal alloy to parts of aluminum salt-containing composition by volume.

The composition may be further configured to substantially reduce hyperhidrosis following two or more applications of the composition to a location on a patient containing at least one sweat gland through ablation of the at least one sweat gland.

The composition may be further configured to substantially reduce hyperhidrosis following a single application of the composition to a location on a patient containing at least one sweat gland through ablation of the at least one sweat gland.

The composition may further include an anhydrous polymer. In one embodiment, all components or ingredients of the composition and the device are anhydrous.

Implementations of sodium compositions may include sodium metal or a sodium and potassium metal alloy where the sodium metal or sodium and potassium metal alloy is coupled to an applicator or a base configured to permit a user to apply the sodium metal or the sodium and potassium metal alloy to: a location in a patient's nose to ablate tissue to reduce nasal discharge, improve airflow, reduce pain symptoms, reduce seasonal allergy symptoms, or any combination thereof; an enlarged gland; adipose tissue containing fat in need of reduction in volume or change in shape; or a cancer lesion or cancer tumor.

Implementations of sodium compositions may include one, all, or any of the following:

The enlarged gland may be selected from the group consisting of prostate gland, pilosebaceous unit, or a sebaceous gland.

This disclosure, its aspects and implementations, are not limited to the specific components, assembly procedures or method elements disclosed herein. Many additional components, assembly procedures and/or method elements known in the art consistent with the intended heat generating systems will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such heat generating systems, and implementing components and methods, consistent with the intended operation and methods.

In places where the description above refers to particular implementations of heat generating systems and implementing components, sub-components, methods and sub-methods, it should be readily apparent that a number of modifications may be made without departing from the spirit thereof and that these implementations, implementing components, sub-components, methods and sub-methods may be applied to other heat generating systems.

What is claimed is:

1. A device, comprising:
a substrate having a first surface and a second surface, and an alkali metal embedded in or integral with the substrate, wherein the alkali metal is a neat alkali metal selected from sodium and potassium, and wherein the neat alkali metal is present in an amount sufficient to generate an amount of heat in situ when the substrate contacts a treatment surface separate from the device to bring the neat alkali metal in contact with water present at the treatment surface, wherein the amount of heat generated is limited by an amount of or moles of water at the treatment surface.

2. The device of claim 1, wherein the first surface of the substrate is a first planar surface and the second surface of the substrate is an opposing planar surface.

3. The device of claim 2, wherein the first planar surface is a contact surface or distal surface for contact with the treatment surface.

4. The device of claim 2, wherein the opposing planar surface is a proximal surface in which the alkali metal is in contact.

5. The device of claim 1, wherein the alkali metal additionally forms a layer on the first surface of the substrate.

6. The device of claim 5, wherein the layer forms a discontinuous layer on the first surface of the substrate.

7. The device of claim 5, wherein the alkali metal additionally forms a discontinuous layer on the second surface of the substrate.

8. The device of claim 1, wherein the substrate is a mesh having open regions and the alkali metal is embedded in a portion of the open regions.

9. The device of claim 1, wherein the amount of heat generated is limited by the amount of or moles of alkali metal selected from sodium and potassium.

10. The device of claim 1, wherein the amount of heat generated is proportional to moles of water present at a point of contact between the alkali metal and the treatment surface.

11. The device of claim 1, wherein the amount of heat generated is limited by the amount of or moles of water at a point of contact between the alkali metal and the treatment surface.

12. The device of claim 1, wherein the amount of heat generated is proportional to an amount of or moles of water at a point of contact between the alkali metal and the treatment surface.

13. The device of claim 1, wherein the alkali metal is neat sodium.

14. The device of claim 13, wherein the amount of heat generated is in proportion to moles of water present at a point of contact between the alkali metal and the treatment surface.

15. The device of claim 1, wherein the alkali metal is an alloy of sodium or an alloy of potassium.

16. The device of claim 15, wherein the alkali metal is a sodium/potassium alloy.

17. The device of claim 1, wherein the substrate is a paste.

18. The device of claim 17, wherein the paste is comprised of an anhydrous aluminum.

19. The device of claim 1, wherein the substrate is a metal substrate or metal alloy substrate.

20. The device of claim 19, wherein the metal substrate is a stainless steel mesh.

21. The device of claim 1, wherein the substrate is a woven substrate.

22. The device of claim 1, wherein the substrate has a water impermeable layer.

23. The device of claim 1, wherein the neat alkali metal is oxidized by water present at the treatment surface.

24. A kit, comprising:
a device according to claim 1;
a wipe comprising a solvent; and instructions for use.

25. The kit of claim 24, wherein the solvent is isopropyl alcohol.

26. The kit of claim 24, further comprising gauze.

27. A medical device, comprising:
a substrate having a first surface and a second surface, and an alkali metal embedded in or integral with the substrate, wherein the alkali metal is a neat alkali metal selected from sodium and potassium, and wherein the neat alkali metal is present in an amount sufficient to generate an amount of heat in situ when the substrate contacts a treatment surface on a human subject to bring the neat alkali metal in contact with water present at the treatment surface.

* * * * *